(12) United States Patent
He et al.

(10) Patent No.: US 11,332,707 B2
(45) Date of Patent: May 17, 2022

(54) ENDOPHYTIC FUNGUS FROM GINGKO, METABOLITE PRODUCT AND USE THEREOF

(71) Applicant: DEZHOU UNIVERSITY, Shandong (CN)

(72) Inventors: Qing He, Dezhou (CN); Qiangcheng Zeng, Dezhou (CN); Lianying Zhang, Dezhou (CN); Zhongmin Dai, Dezhou (CN); Haixia Zhou, Dezhou (CN); Mingyou Wang, Dezhou (CN); Jianzhou Meng, Dezhou (CN)

(73) Assignee: DEZHOU UNIVERSITY, Dezhou (CN)

( * ) Notice: Subject to any disclaimer, the term of this patent is extended or adjusted under 35 U.S.C. 154(b) by 235 days.

(21) Appl. No.: 16/469,830

(22) PCT Filed: Nov. 2, 2018

(86) PCT No.: PCT/CN2018/113709
§ 371 (c)(1),
(2) Date: Jun. 14, 2019

(87) PCT Pub. No.: WO2019/119992
PCT Pub. Date: Jun. 27, 2019

(65) Prior Publication Data
US 2021/0238538 A1    Aug. 5, 2021

(30) Foreign Application Priority Data

Dec. 21, 2017  (CN) .......................... 201711396247.X
Aug. 30, 2018  (CN) .......................... 201811004688.5

(51) Int. Cl.
| C12N 1/14 | (2006.01) |
| A61K 36/06 | (2006.01) |
| C12P 1/02 | (2006.01) |
| C12R 1/77 | (2006.01) |

(52) U.S. Cl.
CPC .............. *C12N 1/145* (2021.05); *A61K 36/06* (2013.01); *C12P 1/02* (2013.01); *C12R 2001/77* (2021.05)

(58) Field of Classification Search
CPC .......... C12N 1/145; C12N 1/14; A61K 36/06; C12R 2001/77; C12P 1/02
See application file for complete search history.

(56) References Cited

FOREIGN PATENT DOCUMENTS

| CN | 102676398 A | * | 9/2012 | .............. C12N 1/14 |
| CN | 102676398 A | | 9/2012 | |
| CN | 107312720 A | | 11/2017 | |
| CN | 108102928 A | | 6/2018 | |
| KR | 20120121076 A | | 11/2012 | |

OTHER PUBLICATIONS

Li et al. Phytotoxic and antibacterial metabolites from Fusarium proliferatum ZS07 isolated from the gut of long-horned grasshoppers. J Agric Food Chem. 2014. 10;62(36):8997-9001.*
Feb. 12, 2019 International Search Report issued in International Patent Application No. PCT/CN2018/113709.
Feb. 12, 2019 Written Opinion issued in International Patent Application No. PCT/CN2018/113709.
Fengmei Chen et al. "Biological Characteristics of Ginkgo Biloba Endophytic Fusarium GI115". Jiangsu Agricultural Sciences, vol. 6, Jun. 30, 2006, pp. 149-151.
B.V. Deepthi et al. "Antifungal Attributes of Lactobacillus Plantarum MYS6 Against Fumonisin Producing Fusarium Proliferatum Associated With Poultry Feeds". PLOS One, Jun. 10, 2016, pp. 1-22.
Yufeng Ji et al. "Experimental Study On Anti-Tumor Effect of Ginkgo Biloba Extract". Traditional Chinese Medicinal Research, vol. 18, No. 7, Jul. 2005, pp. 14-16.
Chengzhang Wang et al. "Antitumor Biological Activity of Polyprenyl Phosphate From Leaves of *Ginkgo biloba* L. In Vivo and In Vitro". Chemistry and Industry of Forest Products, vol. 26, No. 3, Sep. 2006, pp. 13-16.
Jianxin Guo et al. "Isolation and Screening of Anti-Fungal Isolates From Endophytic Fungi in *Gingko biloba* L." Acta Agriculturae Boreali-Occidentalis Sinica, vol. 14, No. 4, 2005, pp. 14-17.
Li Miao et al. "Endophytic Fungi From Four Plant Species: Their Isolation and Antitumor Activity". Microbiology China, vol. 36, No. 6, Jun. 20, 2009, pp. 865-869.
Hiroshi Tsugawa et al. "MS-Dial: Data Independent MS/MS Deconvolution for Comprehensive Metabolome Analysis". Nature Methods, vol. 12, No. 6, Jun. 2015, pp. 523-526.

* cited by examiner

*Primary Examiner* — Lynn Y Fan
(74) *Attorney, Agent, or Firm* — Oliff PLC

(57) ABSTRACT

An endophytic fungus from gingko, that is, *Fusarium proliferatum* DZHQ1 having antitumor activity and antibacterial activity, is isolated from the ginkgo bark. The species of the strain is determined by the combination of colonial morphology and 18 sRNA sequencing, and then the anti-cervical cancer activity of a crude extract of the strain is detected by MTT. Finally, a secondary metabolite of the strain with an inhibition rate of more than 50% is isolated by semi-preparative HPLC, which promotes the further screening of individual compounds with anti-tumor activity. Moreover, the metabolite of the endophytic fungus from gingko shows a more pronounced inhibition in the detection of activity against *E. coli* and/or *S. aureus*, and has potential use in the preparation of new antibacterial products.

8 Claims, 12 Drawing Sheets

ENDOPHYTIC FUNGUS FROM GINGKO, METABOLITE PRODUCT AND USE THEREOF

BACKGROUND

Technical Field

The present invention relates to the field of microorganisms, and specifically to an endophytic fungus from gingko, a metabolite product, and use thereof in anti-tumor and antibacterial applications.

Related Art

The description here merely provides background information related to the present disclosure and does not necessarily constitute the prior art.

Cancer is one of the major diseases that endanger human health today, and it is a serious threat to human life. Cervical cancer is the most common gynecological malignant tumor, and the age of incidence has become younger in recent years. At present, there are more than 50 kinds of anti-tumor drugs commonly used in clinical practice, but most of the drugs can only relieve the disease and fail to achieve the goal of complete cure. Therefore, the development of new anti-tumor drugs has always been a major aspect of drug research.

E. coli is a typical Gram-negative bacillus, and the disease associated therewith is a common disease. The harm caused by E. coli in veterinary clinic is very serious. It can cause disease all year round and leads to common and frequently-occurring diseases plaguing the development of aquaculture, causing serious economic losses to the poultry industry. Drug resistance easily occurs during the treatment process, the drug resistant spectrum is broad, and the drug resistant mechanism is complicated, causing great difficulty to the prevention and treatment of the disease in the poultry industry. Therefore, seeking for an effective component against E. coli has become a research hotspot in recent years.

S. aureus is one of the most common pathogens found with external infection in hospitals. The clinical isolates of bacterial strains obtained by CHINET Bacterial Resistance Monitoring Network in dozens of hospitals in China over the years indicate that S. aureus is one of the top 5 clinical pathogens. The bacteria can cause severe pneumonia, meningitis, bone and joint infections, endocarditis and bacteremia. In particular, patients with burn wound infection, acute liver failure and hematogenous nephritis are susceptible to infection with this bacterium. In recent years, the emergence of S. aureus strains, which have reduced sensitivity to some drugs, cause humans to encounter a dilemma that certain infections are incurable. Therefore, it is important to find an effective component against S. aureus.

Gingko is a special medicinal plant in China. It has been found that gingko leaves contain more than 100 kinds of chemical components, mainly including flavonoids and ginkgolides. The ginkgetin, polypentenol, and others in the extract all have anti-tumor effect. Common gingko extracts include *Ginkgo biloba* leaf extract (EGb), *Gingko biloba* leaf polypentenol (GP), *Gingko biloba* leaf polysaccharides (GBLP), and *Gingko biloba* exocarp polysaccharides (GBEPs). EGb contains various components, mainly including flavonoids and terpenes. Studies show that EGb inhibits both transplanted sarcoma S180 and hepatoma H22 cells in vitro and in vivo in mice (Ji Yufeng et al., Experimental study on anti-tumor effect of *Ginkgo biloba* extract. TRADITIONAL CHINESE MEDICINAL RESEARCH. 2005, 18(7): 14-16). The inhibition rate of GP on human gastric cancer cell line SGC-7901, human colon adenocarcinoma cell line LOVO and human cervical cancer Hela cell line is 60%-80% in vitro, and is 50% to 65% on transplanted tumor cells Heps, S180 and EC in vivo (Wang Chengzhang et al., Antitumor biological activity of polypentenyl phosphate from leaves of *Gingko biloba* L. in vitro and in vivo. CHEMISTRY AND INDUSTRY OF FOREST PRODUCTS. 2006, 26(3): 13-16). GBEP can inhibit the human hepatoma cell line BEL-7404, gastric adenocarcinoma cell line SGC-7901 and lung adenocarcinoma cell line SPC-A-1 in vitro at a dose of 10-320 µg/mL for 24 to 72 h. The possible mechanisms of action of *Gingko biloba* extract against tumors include anti-oxidation effect, scavenging free radicals, affecting the proliferation and induction of apoptosis of tumor cells, inhibiting the tumor vascularization, regulating tumors and related genes, and cytotoxic effects on tumor cells.

However, *Gingko biloba* grows slowly. Under natural conditions, it takes more than 20 years from planting to bearing fruit, which restricts the development of its medicinal effects. According to the symbiotic theory of endophytic fungi in plants, it is likely that there are some endophytic fungi in *Gingko biloba*, which can produce the same or similar chemical components similar to those found in *Gingko biloba*. Therefore, endophytic fungi from gingko have become a research hotspot, and are expected to become a new source of gingko-based drugs or a new way for producing bioactive substances. There are few studies on endophytic fungi from gingko, particularly the research on the anti-tumor activity of endophytic fungi from gingko is much fewer. Guo Jianxin et al. isolated 522 endophytic fungi from gingko of Yangling, Shaanxi Province, and determined their inhibitory effects on 7 plant pathogenic fungi by mycelial growth inhibition method. The results showed that 50.7% of the strains had antibacterial activity (Guo Jianxin et al. Isolation and screening of anti-fungal isolates from endophytic fungi in *Gingko Biloba* L. Acta Agriculturae Boreali-Occidentalis Sinica. 2005, 14(4): 14-17). In vitro anti-tumor tests by Miao Li et al showed that among 19 gingko-derived endophytic fungi isolated from Fuyang, Anhui Province, the most active strain was YXS, and the crude extract of fermentation broth therewith has an inhibition rate ($IC_{50}$) of 18.3, 3.6 and 6.5 µg/ml, respectively for tumor cells EC109, human nasopharyngeal carcinoma HONE1 and human cervical cancer HeLa (Miao Li, Wang Yuanyuan, Zhu Lei, Wu Zhengjun, Zhou Rumei. Endophytic fungi from four plant species: Their isolation and antitumor activity. Microbiology China. 2009, 36(6): 865-869).

The research on the active substances produced by endophytic fungi in gingko has important theoretical significance and potential application value for the development of medicinal endophytic fungi resources and new microbial drugs from gingko in China.

SUMMARY

In view of the problems existing in the prior art described above, studies are carried out on endophytic fungi in gingko in the present disclosure, for the purpose of obtaining an anti-tumor and/or anti-bacterial drug or biologically active substance.

Specifically, the present disclosure relates to the following technical solutions:

In a first typical embodiment of the present disclosure, an endophytic fungus from gingko, that is, *Fusarium prolifera*- tum DZHQ1 is provided, which is deposited in China General Microbiological Culture Collection Center (CGMCC) (Address: No. 3 Courtyard, No. 1, Beichen West Road, Chaoyang District, Beijing) under the CGMCC Accession No. 14983 on Nov. 28, 2017.

In a second typical embodiment of the present disclosure, a method of culturing the endophytic fungus is provided, including activating, culturing or fermenting on a PDA medium.

In a third typical embodiment of the present disclosure, use of the endophytic fungus for the preparation of an antitumor and/or antibacterial active drug is provided, where the tumor is cervical cancer; and the bacteria is *E. coli* and/or *S. aureus*.

In a fourth typical embodiment of the present disclosure, a fermentation broth with the endophytic fungus, and an ethyl acetate extract of the fermentation broth are provided, both of which have antitumor activity and/or antibacterial activity.

Further, a metabolite product of the endophytic fungus from gingko is provided. An ethyl acetate extract of the fermentation broth is dissolved in methanol or water to obtain a metabolite product of the endophytic fungus from gingko, which has antitumor activity and/or antibacterial activity.

In a fifth typical embodiment of the present disclosure, an antitumor and/or antibacterial active composition including a fermentation broth with the endophytic fungus, an ethyl acetate extract of the fermentation broth, and/or a metabolite product of the endophytic fungus from gingko.

In a sixth typical embodiment of the present disclosure, a method of treating a tumor is provided, including a step of treating the tumor using the fermentation broth of the endophytic fungus, the ethyl acetate extract of the fermentation broth, the metabolite product of the endophytic fungus from gingko, and/or the composition, where the tumor is cervical cancer.

In a seventh typical embodiment of the present disclosure, a method of combating a bacterium is provided, including a step of inhibiting the bacterium using the fermentation broth of the endophytic fungus, the ethyl acetate extract of the fermentation broth, the metabolite product of the endophytic fungus from gingko, and/or the composition, where the bacterium is *E. coli* and/or *S. aureus*.

Compared with the related art known to the inventors, one of the technical solutions of the present disclosure has the following beneficial effects:

In the present invention, an endophytic fungus from gingko, that is, *Fusarium proliferatum* DZHQ1 having anti-cervical cancer activity, is isolated from the ginkgo bark. The species of the strain is determined by the combination of colonial morphology and 18 sRNA sequencing, and then the anti-cervical cancer activity of a crude extract of the strain is detected by MTT. Finally, a secondary metabolite of the strain with an inhibition rate of more than 50% is isolated by semi-preparative HPLC, which promotes the further screening of individual compounds with anti-tumor activity.

Moreover, the metabolite of the endophytic fungus from gingko disclosed in the present invention shows a more pronounced inhibition in the detection of activity against *E. coli* and/or *S. aureus*, and has potential use in the preparation of new antibacterial products.

BRIEF DESCRIPTION OF THE DRAWINGS

The accompanying drawings constituting a part of the disclosure are provided for further illustrating the present disclosure. The illustrative embodiments of the present disclosure and the description thereof are intended to explain the present disclosure and do not constitute an undue limitation on the present disclosure.

DETAILED DESCRIPTION

Figure 1:
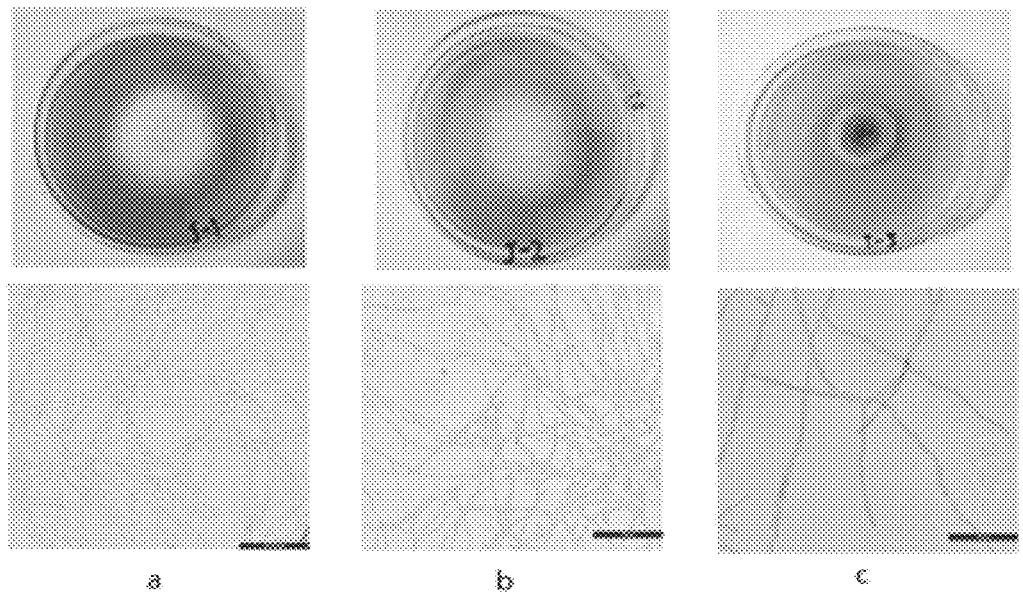
FIG. 1 shows colonial and mycelial morphologies of three stains of endophytic fungi from gingko, in which a: Strain J-1; b: Strain J-2; and c: Strain J-3.

It should be noted that the following detailed description is exemplary and is intended to provide a further description of the present disclosure. All technical and scientific terms used herein have the same meaning as commonly understood by one of ordinary skill in the art to which this disclosure belongs, unless otherwise indicated.

It is to be noted that the terminology used herein is for the purpose of describing particular embodiments, and is not intended to limit the exemplary embodiments of the present disclosure. As used herein, the singular terms are also intended to include the plural, and it is also to be understood that when the terms "include" and/or "comprise" are used in the specification, they indicate the presence of features, steps, operations and/or combinations thereof, unless otherwise indicated.

As described in the background art, the development of new anti-tumor and/or antibacterial drugs in the prior art has always been a major aspect in the field of drug research. After the research and exploration of endophytic fungi in gingko by the present inventor, an endophytic fungus from gingko, that is, *Fusarium proliferatum* DZHQ1 is provided, which is deposited in China General Microbiological Culture Collection Center (CGMCC) (Address: No. 3 Courtyard, No. 1, Beichen West Road, Chaoyang District, Beijing) under the CGMCC Accession No. 14983 on Nov. 28, 2017.

In a first typical embodiment of the present disclosure, a method of culturing the endophytic fungus is provided, including activating, culturing or fermenting on a PDA medium.

In another typical embodiment of the present disclosure, use of the endophytic fungus for the preparation of an antitumor and/or antibacterial active drug is provided.

Further, the tumor is cervical cancer; and the bacterium is E. coli and/or S. aureus.

In another typical embodiment of the present disclosure, a fermentation broth with the endophytic fungus, or an ethyl acetate extract of the fermentation broth is provided, both of which have antitumor activity and/or antibacterial activity, and can be used in the preparation of relevant anti-tumor or anti-bacterial products having particularly therapeutic activity for cervical cancer and inhibition on E. coli and/or S. aureus.

Further, a metabolite product of the endophytic fungus from gingko is provided. An ethyl acetate extract of the fermentation broth is dissolved in methanol or water (in about 5-30 min) to obtain a metabolite product of the endophytic fungus from gingko, which has also antitumor activity and/or antibacterial activity, and can be used in the preparation of relevant anti-tumor or anti-bacterial products in the form of pharmaceutical preparation or other preparations having particularly therapeutic activity for cervical cancer and inhibition on E. coli and/or S. aureus.

In a specific embodiment of the present disclosure, the metabolite product of endophytic fungus from gingko dissolved in methanol can combat E. coli.

In another specific embodiment of the present disclosure, the metabolite product of endophytic fungus from gingko dissolved in methanol or water can combat E. coli and/or S. aureus.

Further, the fermentation broth of the endophytic fungus, the ethyl acetate extract of the fermentation broth, or the metabolite product of the endophytic fungus from gingko has a composition including, without limitation, betaine, scopoletin, harmine, rosmarinic acid, oxipurinol, resveratrol, naringenin, catechin, taxifolin, and xanthohumol.

Still further, the active ingredients in the metabolite product of the endophytic fungus from gingko dissolved in methanol include, but are not limited to, betaine, scopoletin, harmine, rosmarinic acid, oxipurinol, resveratrol, naringenin, catechin, taxifolin and xanthohumol.

Still further, the betaine, scopoletin, harmine, rosmarinic acid, oxipurinol, resveratrol, naringenin, catechin, taxifolin, and xanthohumol are substance represented by peaks having a peak area of $10^5$ or higher in the HPLC chromatogram of the metabolite product of the endophytic fungus from gingko.

In one or some specific embodiment(s) of the present disclosure, the metabolite product of endophytic fungus from gingko is as shown in column 6 or 7 of Table 3.

In one or some specific embodiment(s) of the present disclosure, a method for preparing the ethyl acetate extract of the fermentation broth is provided. The method includes: picking up the endophytic fungus cultured in the PDA solid medium, inoculating the mycelial pellets in a PDA liquid medium, culturing for 5-7 days in a shaker at 100-150 r/min at 20-28° C., then adding ethyl acetate at a volume ratio of 1:1-2:1 (where the ratio of ethyl acetate to fermentation broth was 1:1-2:1), culturing in the shaker for another 4 8 days, filtering the fermentation broth to remove mycelium, separating to obtain the organic phase containing the secondary metabolite of the endophytic fungus from gingko, recovering ethyl acetate to obtain a concentrated solution containing the secondary metabolite of the endophytic fungus from ginkgo, and finally, drying the concentrate to obtain an ethyl acetate extract of the fermentation broth.

The PDA solid medium and the PDA liquid medium are conventional potato medium in the prior art, and the formula may include, without limitation, potato 200 g, glucose 20 g, agar 15-20 g and water 1000 mL; or potato 200 g, glucose 20 g and water 1000 mL.

In one or some specific embodiment(s) of the present disclosure, when the metabolite product of the endophytic fungus from gingko is prepared, the ratio of ethyl acetate extract to methanol or water is (0.01-0.05) g:1 mL, and further 0.02 g:1 mL.

In one specific embodiment of the present disclosure, when the metabolite product of the endophytic fungus from gingko is prepared, the system is filtered after dissolution, where the pore size of the filter membrane is 0.22 μm.

In another typical embodiment of the present disclosure, an antitumor and/or antibacterial active composition including a fermentation broth with the endophytic fungus, an ethyl acetate extract of the fermentation broth, and/or a metabolite product of the endophytic fungus from gingko.

Further, the composition further includes a pharmaceutically acceptable carrier that is one or more selected from the group consisting of a diluent, a dispersing agent, a stabilizer, a disintegrating agent, and a lubricant, such as starch, sodium carboxymethylcellulose, glycerin, and the like.

In another embodiment of the present disclosure, a method of treating a tumor is provided, including a step of treating the tumor using the fermentation broth of the endophytic fungus, the ethyl acetate extract of the fermentation broth, the metabolite product of the endophytic fungus from gingko, and/or the composition, where the tumor is cervical cancer.

A method of combating a bacterium is provided, including a step of inhibiting the bacterium using the fermentation broth of the endophytic fungus, the ethyl acetate extract of the fermentation broth, the metabolite product of the endophytic fungus from gingko, and/or the composition, where the bacterium is E. coli and/or S. aureus.

To enable those skilled in the art to more clearly understand the technical solutions of the present disclosure, the technical solutions of the present invention will be described in detail below in conjunction with specific examples.

Example 1: Screening and Identification of Endophytic Fungi from Gingko

Material for separation: Gingko was harvested from Linyi, Shandong Province. The material taken was the bark from the trunk at about 2 cm from the ground, and the thickness was about 3-8 mm. The gingko was about 30 years old and the trunk diameter was about 55 cm. Fresh gingko bark collected was washed with distilled water, and then slightly dried. The outer skin was removed, and the xylem was cut into small sections of suitable length, which were then soaked in 75% ethanol for 6 min, rinsed 2-3 times with sterile water, and dried by sterile filter paper. Then, the section was cut into small pieces and put on a PDA medium containing streptomycin and penicillin, and incubated for 3-20 days in an incubator at 25° C. The mycelia were grown around the medium, and then transferred to a new PDA medium, and continuously incubated in the incubator at 25° C. The incubation was continued until the colonies that grew up were identified as pure bacteria. The purified strain was stored in a tube containing 10% sterile glycerol at −80° C. Three strains of purified endophytic fungi (J-1, J-2, J-3, respectively, named by inventors) were isolated, and 10 ml of a fermentation broth of each strain was taken and shipped to Biosune Biotechnology (Shanghai). Co., Ltd. for 18 sRNA sequencing.

Figure 2:
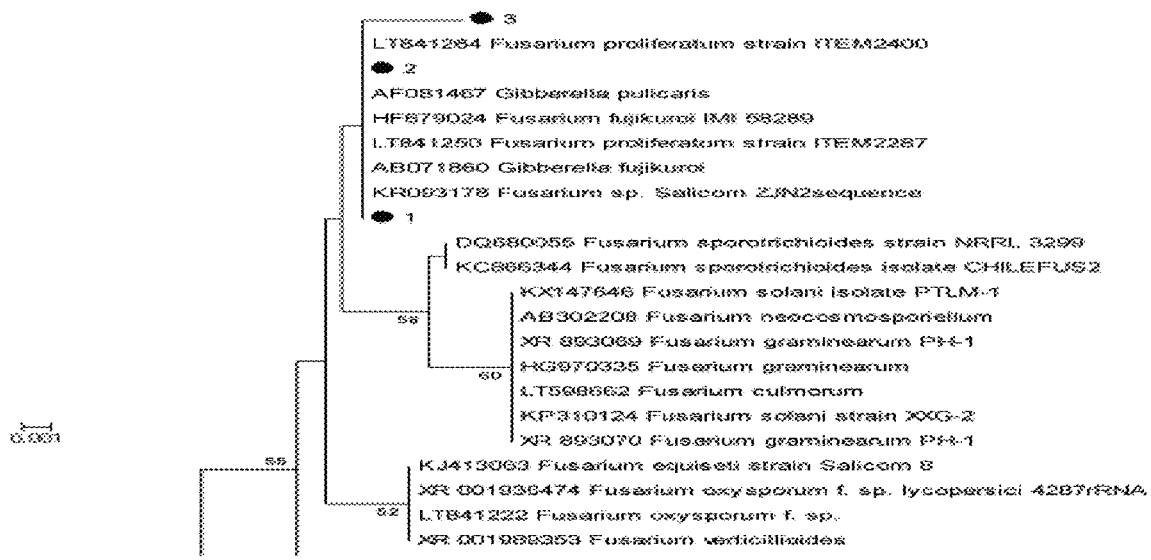
FIG. 2 shows phylogenetic trees of three stains of endophytic fungi from gingko, in which 1: Strain J-1; 2: Strain J-2; and 3: Strain J-3.

FIG. 1 shows colonial morphologies of the three stains of endophytic fungi. FIG. 2 shows phylogenetic trees of the three stains of endophytic fungi from gingko. The similarities between the 18 sRNAs of Strains J-1 and J-2 and *Fusarium proliferatum* are 99% and 98%, respectively, which shows, together with the results of colony characteristics, that Strains J-1 and J-2 belong to the genus *Fusarium* (as shown in FIGS. 1 and 2). The similarity between the 18 sRNA sequence of J-3 and the conserved sequence of the genus *Fusarium* is only 97%. Therefore, it is presumed that Strain J-3 may also belong to the genus *Fusarium*, but this needs to be further confirmed by observation of spore morphology or even by other molecular biological means Example 2: Studies on Antitumor Activity of Endophytic Fungi from Gingko Preparation of fermentation broth and crude mycelium extract: Three strains of gingko-derived endophytic fungi cultured in PDA solid medium were picked up, and the mycelial pellets were inoculated into an Erlenmeyer flask containing 250 ml PDA liquid medium and cultured for 7 days in a shaker at 120 r/min and 20° C. Then, ethyl acetate was added to each flask at a volume ratio of 1:1, and the incubation was continued for 4 days in the shaker. The fermentation broth was filtered through 3-4 layers of gauze to remove the mycelia, and the broth was layered by a separatory funnel to obtain an organic phase containing the secondary metabolites of the endophytic fungus from gingko. Most of the ethyl acetate in the organic phase was recovered using a rotary evaporator to obtain a concentrate containing the secondary metabolites of the endophytic fungus from gingko. Finally, the concentrate was completely dried by a vacuum concentration dryer, to obtain an ethyl acetate extract of the fermentation broth, which was dissolved in DMSO to obtain a crude mycelium extract.

MTT assay for anti-cervical cancer activity of crude extract: Cervical cancer HeLa cell line was used. The cell culture medium was 10% newborn calf serum, 89% RPMI1640 complete medium, and 1% double antibodies (penicillin-streptavidin). The cells were cultured and subcultured in an incubator at 37° C. with 5% $CO_2$, and the anti-cervical cancer activity of the crude extract was determined by MTT assay. The tumor cells in the logarithmic growth phase were digested with trypsin, prepared into a cell suspension in a complete medium, and counted on a hemocytometer. Then 100 µL was inoculated into a 96-well plate, leaving two wells as blank controls. After incubating for 48 h in an incubator at 37° C. with 5% $CO_2$, 20 µL of the sample diluted with the complete medium was added (where for the negative control group, 20 µL of the culture medium was added, for the blank group, 100 µL of the culture medium was added, and 3 replicates were set for each sample). After the culture was continued for another 2 days, the medium in the well was aspirated and discarded. 20 µL of 2.5 µg/µL MTT solution was added to each well, and reacted at 37° C. for 4 h. Then 100 µL of DMSO was added to each well, and allowed to dissolve at 37° C. for 30 min. The absorbency of each well (at a detection wavelength of 570 nm) was measured on a microplate reader. Finally, the inhibition rate is calculated as follows: Inhibition rate=(OD value of negative control−OD value of test group)/(OD value of negative control−OD value of blank control)×100%.

Figure 3:
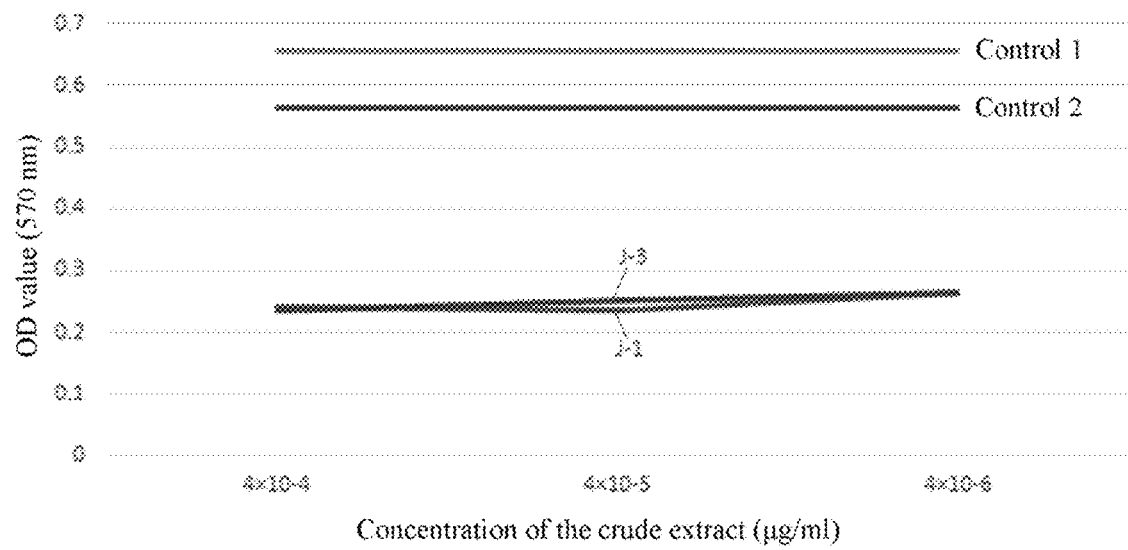
FIG. 3 shows MTT assay for anti-cervical cancer activity of Strains J-1 and J-3 (over 24 h treatment).

The test results of the anti-cervical cancer activity of the crude extract of the fermentation broth (FIG. 3) show that the inhibition rates of Strain J-1 and J-3 on cervical cancer cells were 59.6% and 59.1%, respectively, while the inhibition rate of J-2 was only 13.3%. Therefore, Strain J-1 and J-3 were carried on for further test.

Strain J-1 with high activity against cervical cancer was deposited with the China General Microbiological Culture Collection Center (CGMCC) (Address: Institute of Microbiology, Chinese Academy of Sciences, No. 3 Courtyard, No. 1, Beichen West Road, Chaoyang District, Beijing, 100101) having the Deposit Designation *Fusarium proliferatum* DZHQ1 under the CGMCC Accession No. 14983 on Nov. 28, 2017.

Example 3: Studies on Compounds Having Antitumor Activity Produced by Endophytic Fungi from Gingko Separation of secondary metabolites of endophytic fungus from gingko by semi-preparative HPLC analysis: The column was a C18 column (250 mm×10 mm, 5 µm) and the mobile phase was methanol-water. Eluant: 20% methanol, volume flow rate: 1.0 ml/min, detection wavelength: 210 nm, column temperature 35° C., and injection volume 100 µl. Different substances were separated according to the peak shapes of different secondary metabolites of the strain. Each substance was co-incubated with the cervical cancer HeLa cells, and effective anti-cervical cancer active substances were determined by MTT assay.

Figure 4:
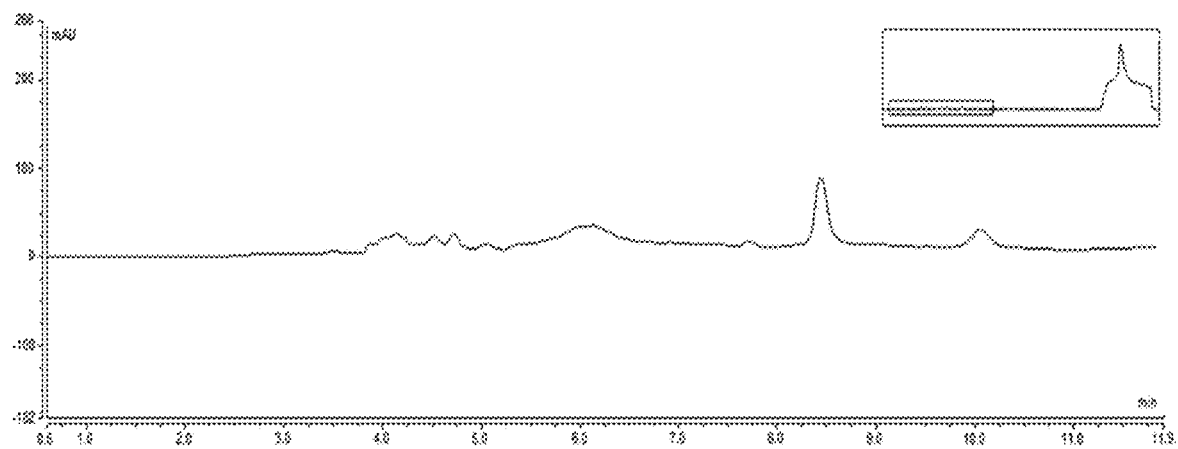
FIG. 4 shows a HPLC chromatogram of a secondary metabolite of Strain J-1.
Figure 5:
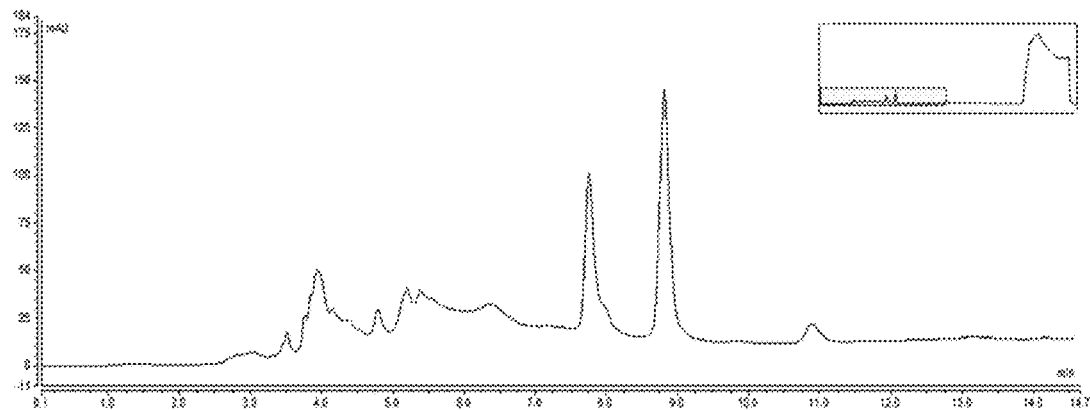
FIG. 5 shows a HPLC chromatogram of a secondary metabolite of Strain J-3.

The secondary metabolites of Strains J-1 and J-3 were separated by semi-preparative HPLC. The results of are shown in FIGS. 4 and 5. From the peaks on the semi-preparative HPLC chromatograms (FIGS. 4 and 5), it can be seen that the secondary metabolites of Strain J-1 and J-3 are different and both contain many substances. Compounds represented by each of the peaks were collected and subjected to MTT assay to determine individual compounds having antitumor activity against cervical cancer.

Example 4

A method for preparing an ethyl acetate extract of a fermentation broth was as follows. Gingko-derived endophytic fungus cultured in PDA solid medium was picked up, and the mycelial pellets were inoculated into an Erlenmeyer flask containing 250 ml PDA liquid medium and cultured for 7 days in a shaker at 120 r/min and 20° C. Then, ethyl acetate was added to each flask at a volume ratio of 1:1, and the incubation was continued for 4 days in the shaker. The fermentation broth was filtered through 3-4 layers of gauze to remove the mycelia, and the broth was layered by a separatory funnel to obtain an organic phase containing the secondary metabolites of the endophytic fungus from gingko. Most of the ethyl acetate in the organic phase was recovered using a rotary evaporator to obtain a concentrate containing the secondary metabolites of the endophytic fungus from gingko. Finally, the concentrate was completely dried by a vacuum concentration dryer, to obtain an ethyl acetate extract of the fermentation broth. The endophytic fungus from gingko is gingko-derived endophytic fungus *Fusarium proliferatum* DZHQ1, deposited under CGMCC Accession No. 14983, in which the sample 17[#] corresponds to Strain J-1. Alternatively, the endophytic fungus from gingko is Strain J-2 of 18[#].

A method for preparing a metabolite product of an endophytic fungus from gingko was as follows. The ethyl acetate extract of the fermentation broth was dissolved in methanol at a ratio of the ethyl acetate extract of the fermentation broth to the methanol of 0.02 g: 1 mL. The solution obtained after 10 min of dissolution is the metabolite product of the endophytic fungus from gingko.

Example 5

A method for preparing a metabolite product of an endophytic fungus from gingko was as follows. The ethyl acetate extract of the fermentation broth in Example 4 was dissolved in water at a ratio of the ethyl acetate extract of the fermentation broth to the water of 0.02 g/mL.

The endophytic fungus from gingko is gingko-derived endophytic fungus *Fusarium proliferatum* DZHQ1, deposited under CGMCC Accession No. 14983, in which the sample 17# corresponds to Strain J-1.

Example 6

A method for preparing a metabolite product of an endophytic fungus from gingko was as follows. The ethyl acetate extract of the fermentation broth in Example 4 was dissolved in methanol or water at a ratio of the ethyl acetate extract of the fermentation broth to the methanol or water of 0.02 g/mL. After 10 min of dissolution, the solution was filtered through a 0.22 μm filter membrane to obtain the metabolite product of the endophytic fungus from gingko. The endophytic fungus from gingko is gingko-derived endophytic fungus *Fusarium proliferatum* DZHQ1, deposited under CGMCC Accession No. 14983, in which the 17# corresponds to Strain J-1. Alternatively, the endophytic fungus from gingko is Strain J-2 of 18#. Finally, the sample 17#, that is, a metabolite product of a gingko-derived endophytic fungus dissolved in methanol or a metabolite product of a gingko-derived endophytic fungus dissolved in water; and the sample 18#, that is, a metabolite product of a gingko-derived endophytic fungus dissolved in methanol or a metabolite product of a gingko-derived endophytic fungus dissolved in water were obtained.

Example 7

A method for preparing a metabolite product of an endophytic fungus from gingko was as follows. Gingko-derived endophytic fungus *Fusarium proliferatum* DZHQ1 cultured in PDA solid medium was picked up, and the mycelial pellets were inoculated into an Erlenmeyer flask containing 250 ml PDA liquid medium and cultured for 6 days in a shaker at 100 r/min and 25° C. Then, ethyl acetate was added to each flask at a volume ratio of 2:1, and the incubation was continued for 3 days in the shaker. The fermentation broth was filtered through 3-4 layers of gauze to remove the mycelia, and the broth was layered by a separatory funnel to obtain an organic phase containing the secondary metabolites of the endophytic fungus from gingko. Most of the ethyl acetate in the organic phase was recovered using a rotary evaporator to obtain a concentrate containing the secondary metabolites of the endophytic fungus from gingko. Finally, the concentrate was fully dried by a vacuum concentration drier, to obtain an ethyl acetae extract of the fermentation broth. The ethyl acetate extract of the fermentation broth was dissolved in methanol at a ratio of the ethyl acetate extract of the fermentation broth to the methanol or water of 0.02 g/mL. The solution obtained after 10 min of dissolution is the metabolite product of the endophytic fungus from gingko.

Example 8

A method for preparing a metabolite product of an endophytic fungus from gingko was as follows.

Three strains of gingko-derived endophytic fungi cultured in PDA solid medium were picked up, and the mycelial pellets were inoculated into an Erlenmeyer flask containing 250 ml PDA liquid medium and cultured for 8 days in a shaker at 140 r/min and 28° C. Then, ethyl acetate was added to each flask at a volume ratio of 1.5:1, and the incubation was continued for 5 days in the shaker. The fermentation broth was filtered through 3-4 layers of gauze to remove the mycelia, and the broth was layered by a separatory funnel to obtain an organic phase containing the secondary metabolites of the endophytic fungus from gingko. Most of the ethyl acetate in the organic phase was recovered using a rotary evaporator to obtain a concentrate containing the secondary metabolites of the endophytic fungus from gingko. Finally, the concentrate was fully dried by a vacuum concentration drier. The ethyl acetate extract of the fermentation broth was dissolved in methanol at a ratio of the ethyl acetate extract of the fermentation broth to the methanol or water of 0.02 g/mL. The solution obtained after 10 min of dissolution is the metabolite product of the endophytic fungus from gingko.

Example 9. Untargeted Metabolomic Detection by LC-MS 1.1. Materials 1.1.1. Basic Information of Samples Two groups of samples (ethyl acetate extract of the fermentation broth in Example 2 or 5) (17 #, 18 #) are set, each group has 2 samples, and there are a total of 4 samples (17-1, 17-2, 18-1, and 18-2).

1.1.2. Reagents water (Watsons), reagents: acetonitrile (Fisher) and formic acid (Sigma-Aldrich) for mass spectrometry 1.1.3. Instruments

| Instrument information table 1 | | | |
|---|---|---|---|
| Instrument | English name | Model and specification | Manufacturer |
| Vortex | vortex | QL-901 | Haimen Qi-lab Instrument Manufacturing Co., Ltd |
| High speed benchtoprefrigerated centrifuge | high speed benchtoprefrigerated centrifuge | Mikro 220R | Hettich |
| MS | MS | Q Exactive ™ Plus Hybrid Quadrupole-Orbitrap ™ Mass Spectrometer | Thermo |
| LC | LC | UltiMate 3000 UHPLC | Thermo |

1.2. Method 1.2.1. Extract of Metabolites

The sample was dissolved in 10 min by adding 1 mL of methanol (sample: methanol=0.02 g: 1 mL), and injected after passing through a 0.22 μm filter membrane.

1.2.2. Liquid Chromatography-Mass Spectrometry Conditions

The analytical instrument for this experiment is Q Exactive plus, Thermo, and the ion source is ESI.

1. Chromatographic Conditions

The column is Waters Atlantis T3 (100×3 mm, 1.8 mm). The column temperature is 35° C. The flow rate is 0.500 [ml/min].

The mobile phase: A. Equate="0.1 v/v % HCOOH—$H_2O$"

D. Equate="acetonitrile"

The chromatographic conditions are shown in a Table below:

TABLE 2

| Time (min) | Parameter |
|---|---|
| 0 | A: 5% D: 95% |
| 0:5 | A: 5% D: 95% |
| 7 | A: 35% D: 65% |
| 8 | A: 90% D: 10% |
| 9.5 | A: 90% D: 10% |
| 11 | A: 5% D: 95% |
| 11 | A: 5% D: 95% |

2. Mass Spectrometry Conditions

Scan range m/z 80-1200;

Resolution: 70,000;

Spectrum data type: Profile;

Capillary voltage: 4000 V (positive) and 3500 V (negative);

Capillary Temp: 350° C.

2. Results and Analysis 2.1. Cation Chromatography

Figure 6:
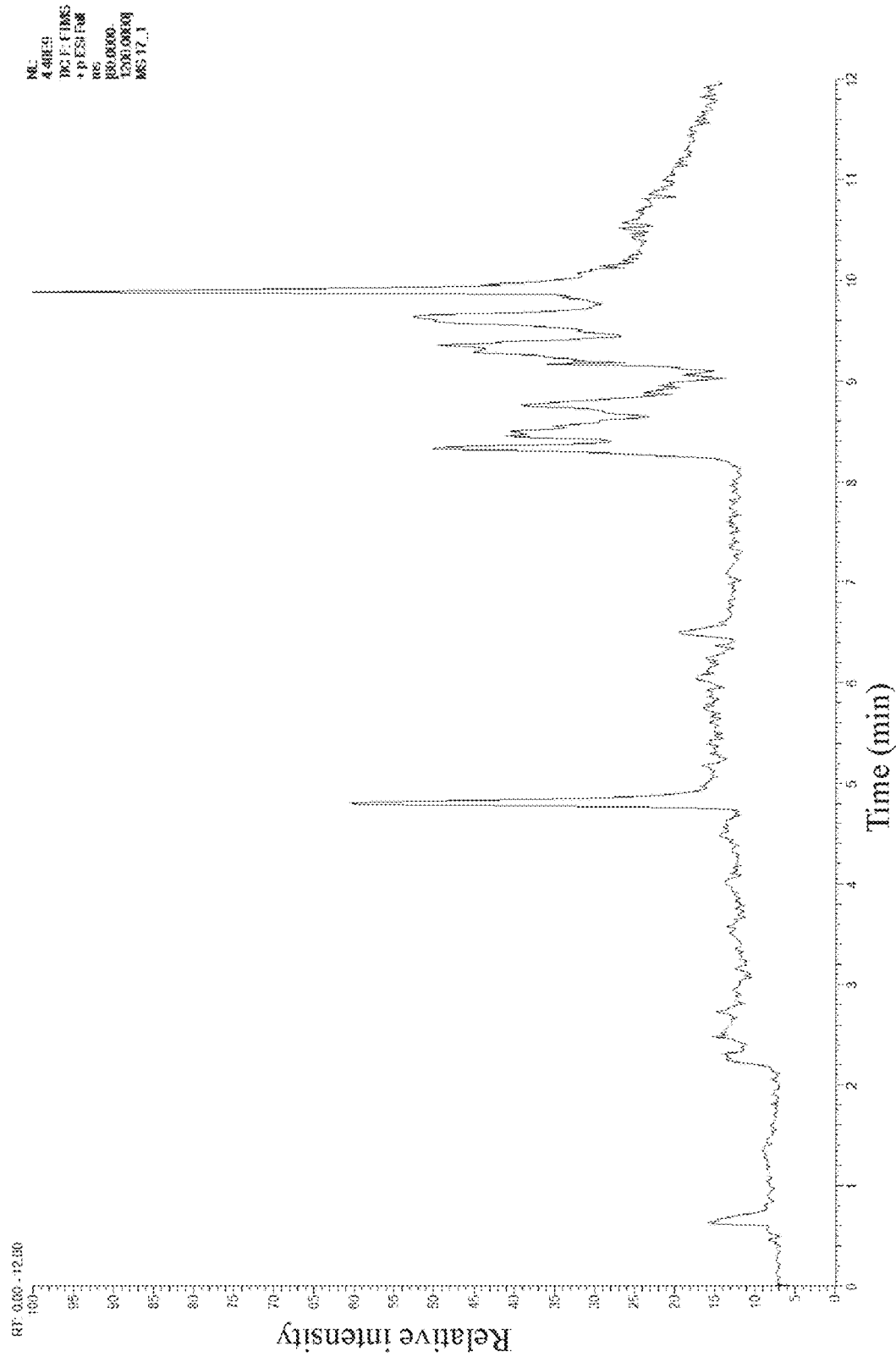
FIG. 6 shows a cation chromatogram of sample $17^\#$ (17-1 and 17-2).
Figure 6:
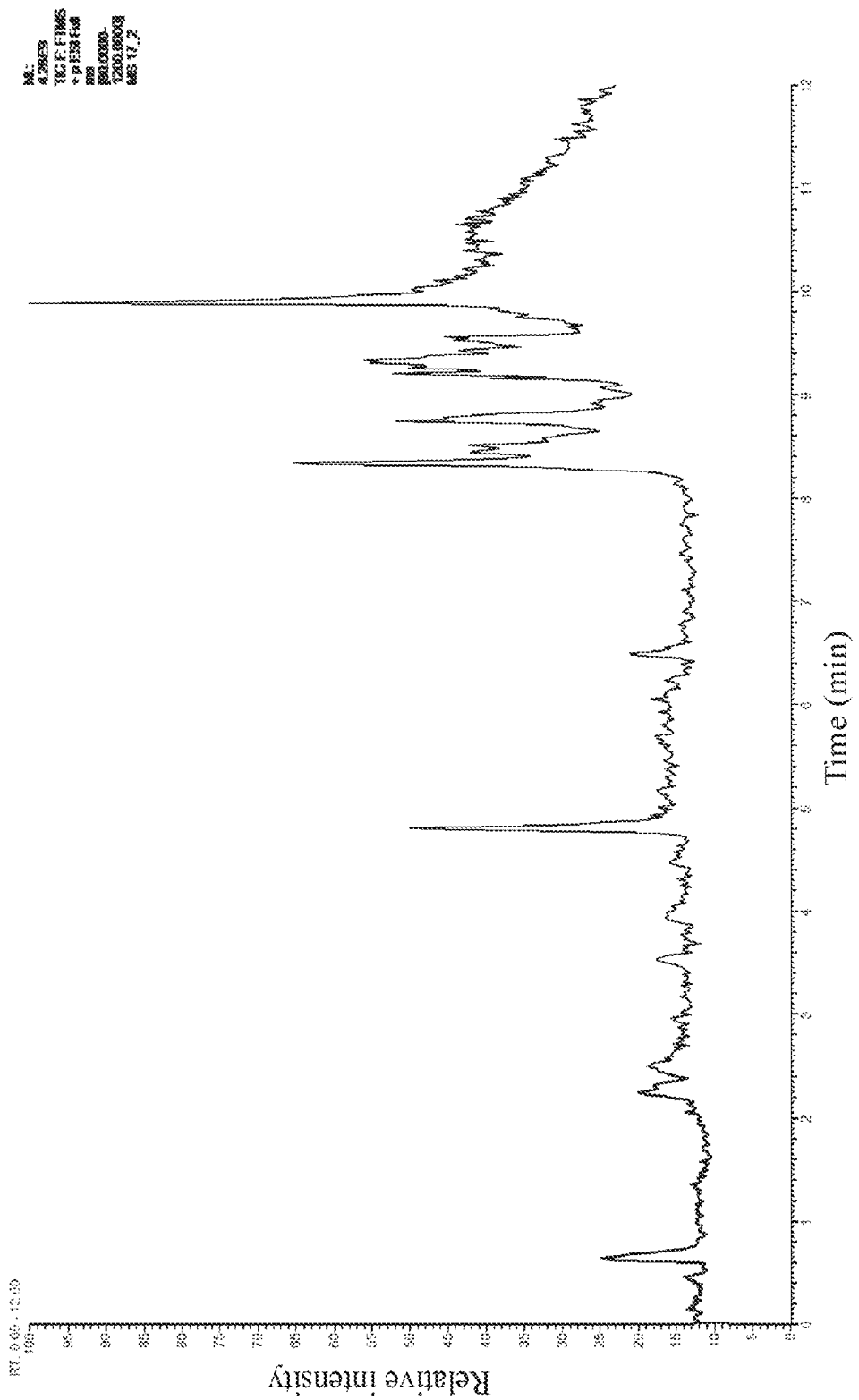
Figure 7:
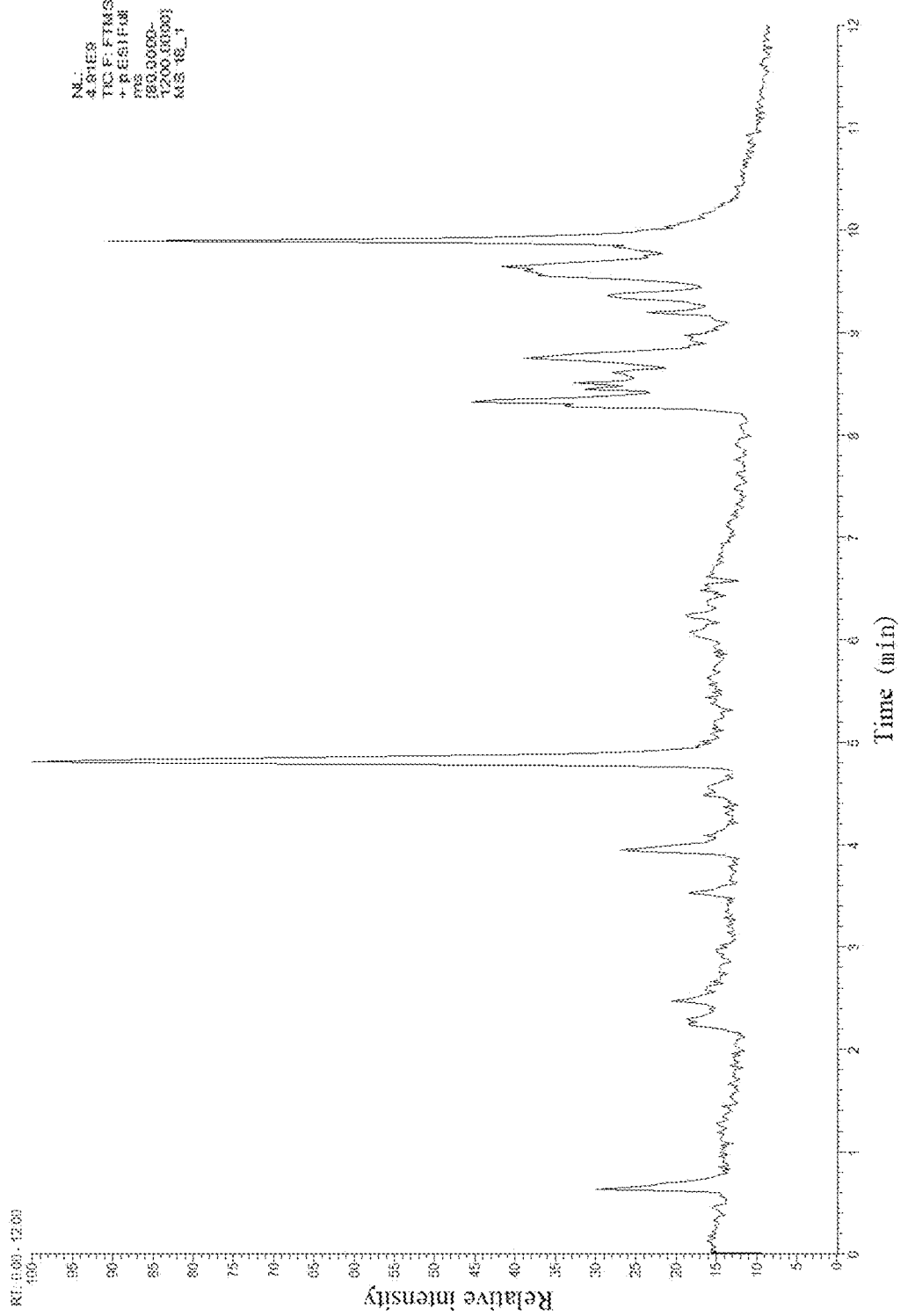
FIG. 7 shows a cation chromatogram of sample $18^\#$ (18-1 and 18-2).
Figure 7:
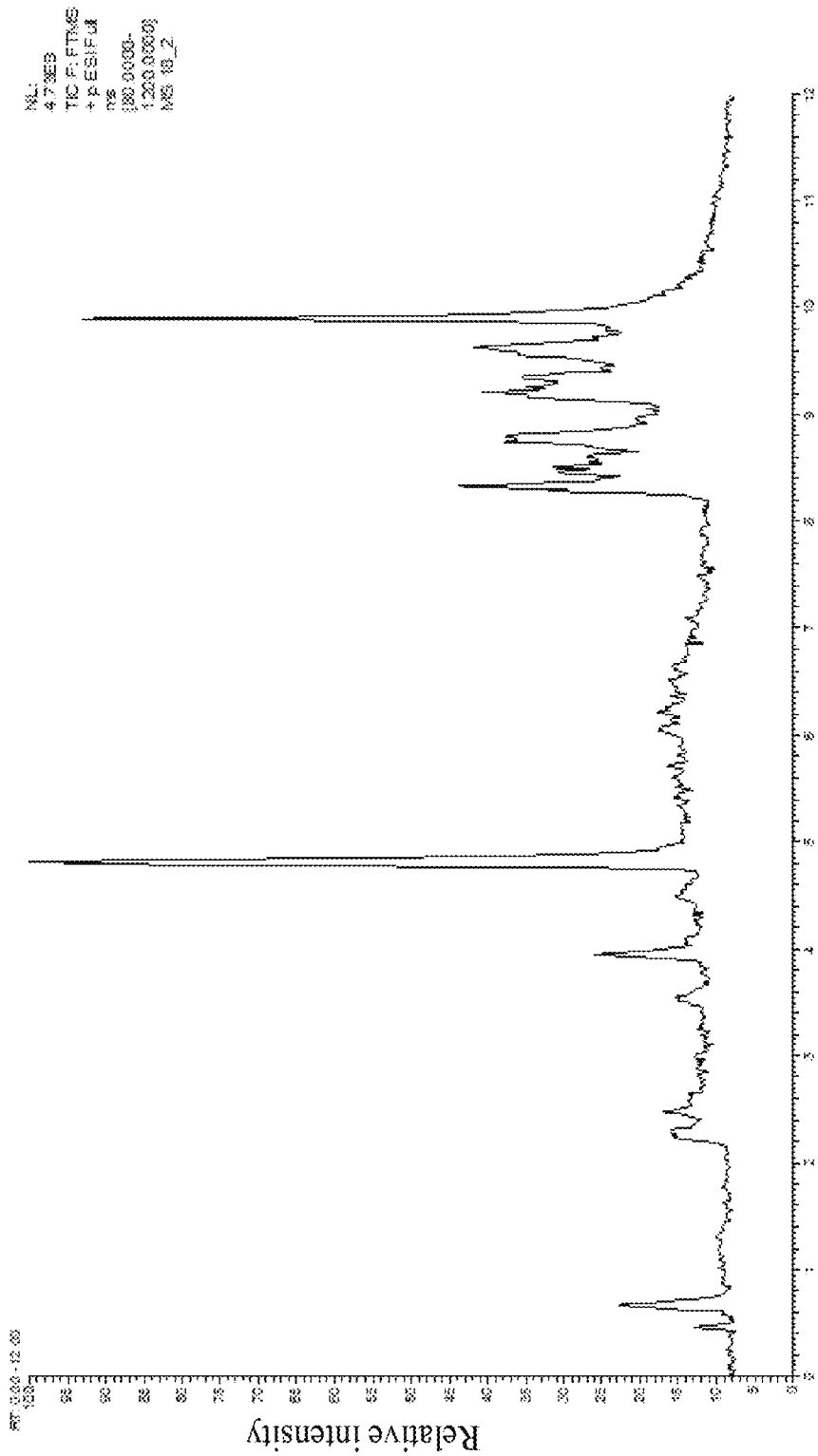

See FIGS. 6 and 7.

2.2. Anion Chromatography

Figure 8:
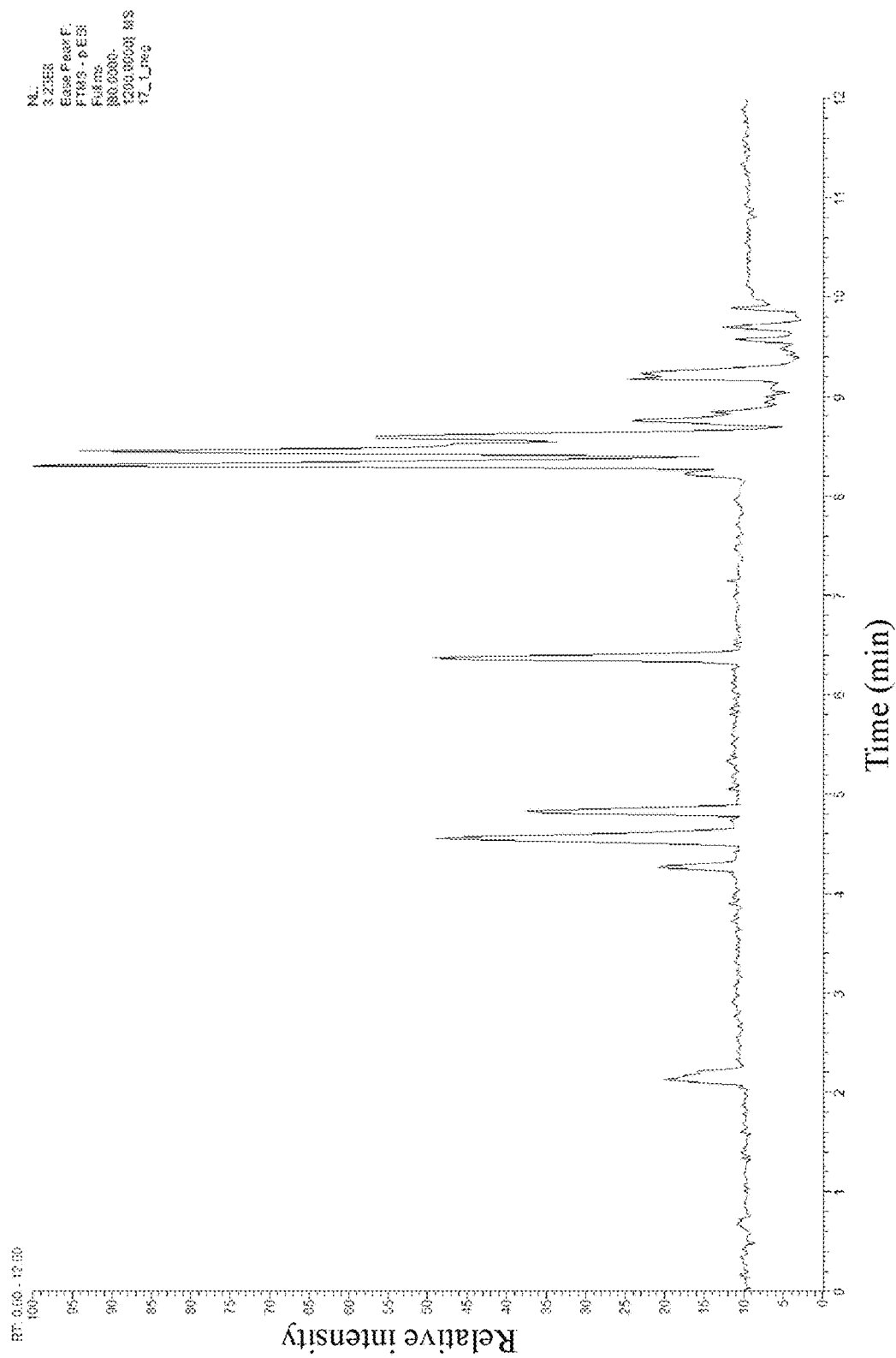
FIG. 8 shows an anion chromatogram of sample $17^\#$ (17-1 and 17-2).
Figure 8:
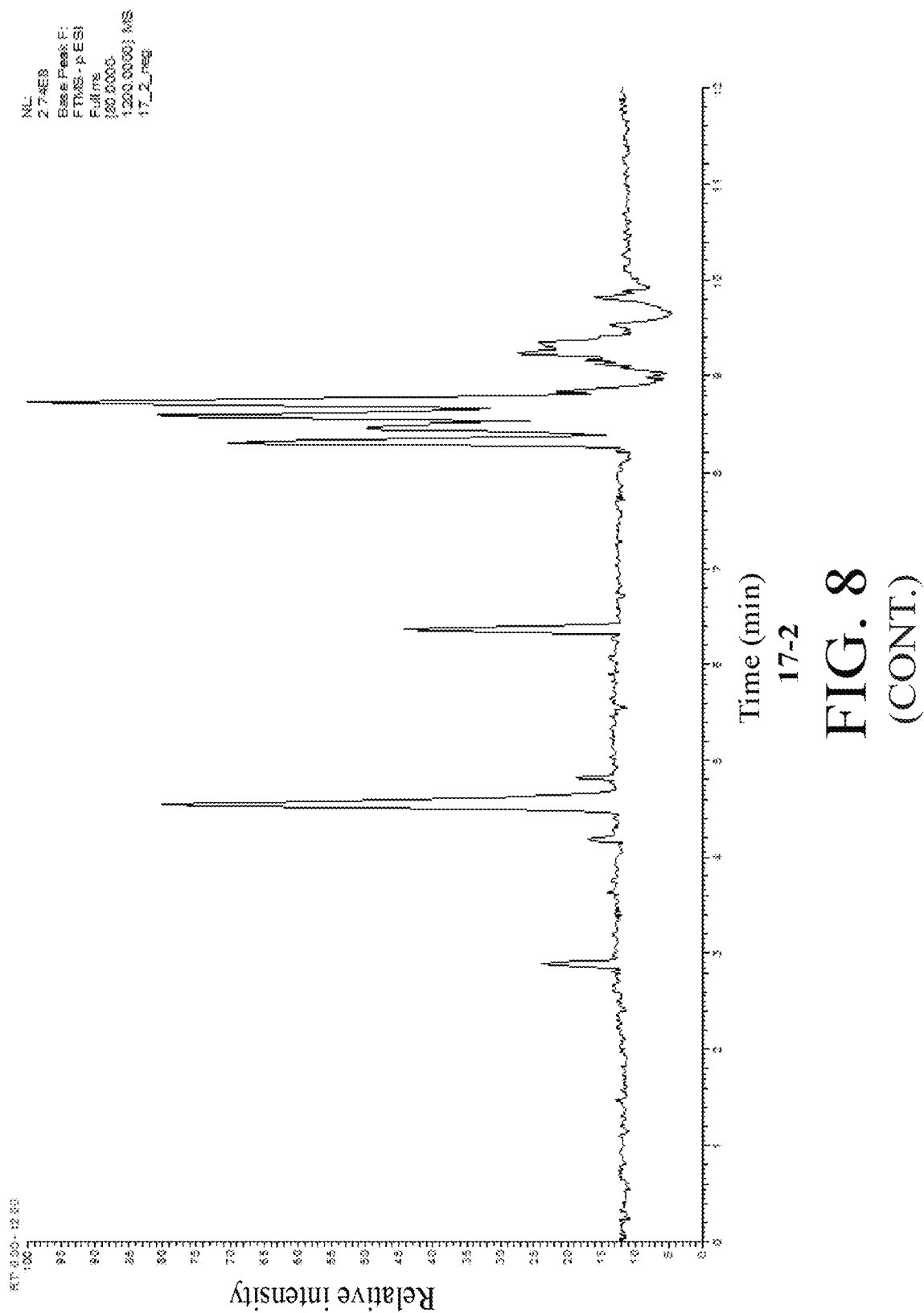
Figure 9:
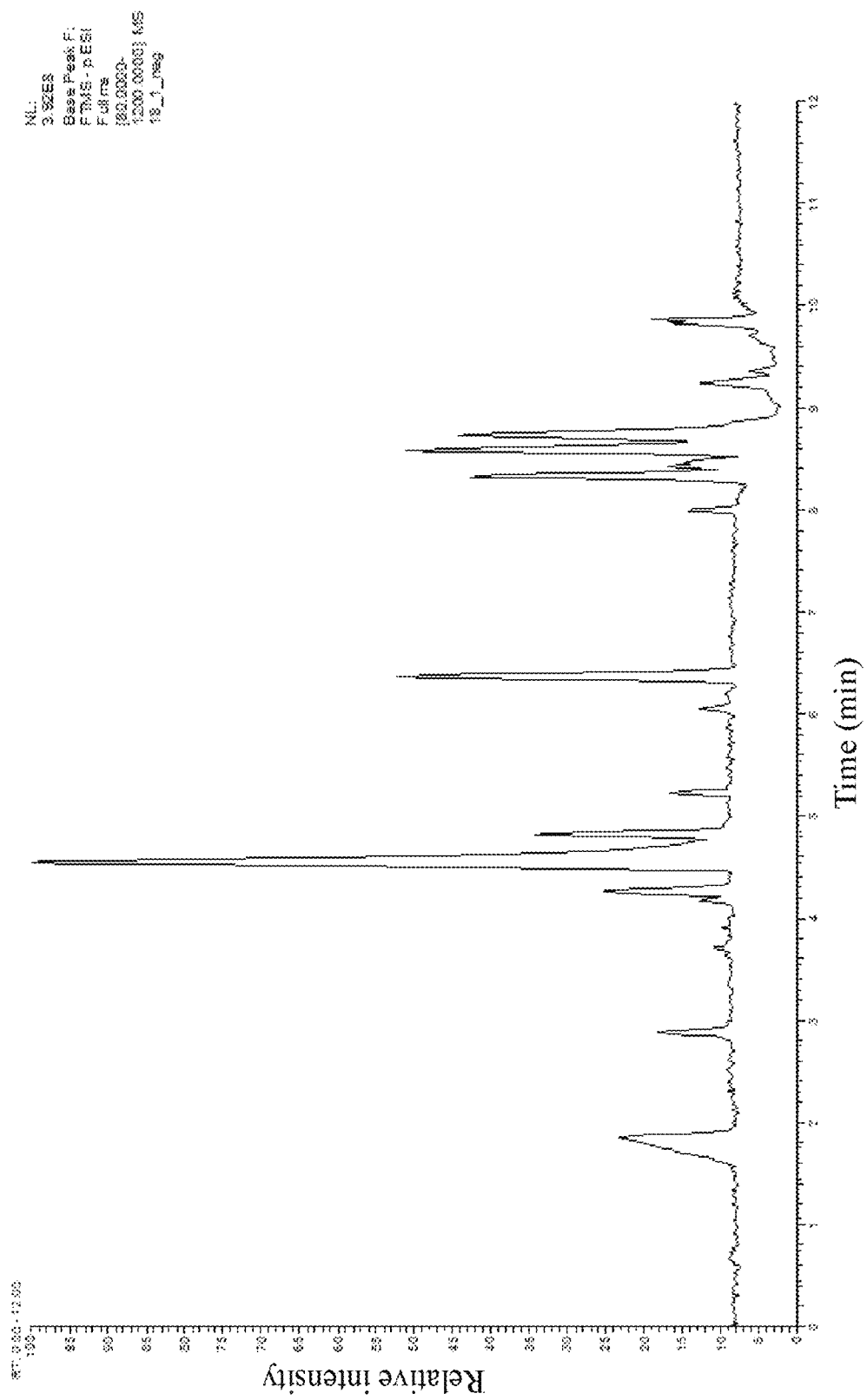
FIG. 9 shows an anion chromatogram of sample $18^\#$ (18-1 and 18-2).
Figure 9:
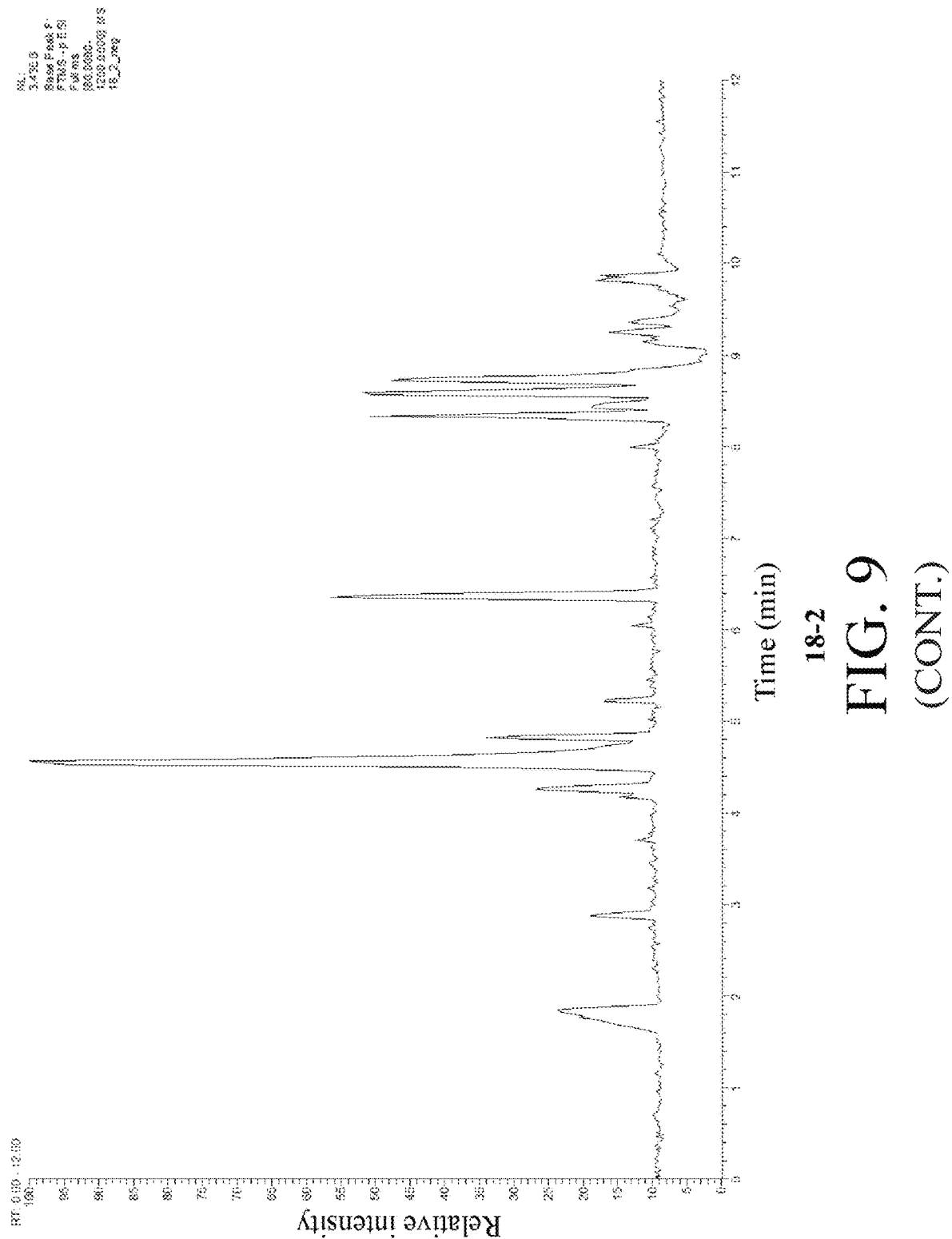

See FIGS. 8 and 9.

2.3. Compound Identification

The raw data from LC-MS is input into MS-DIAL 2.76 (MS-DIAL: data independent MS/MS deconvolution for comprehensive metabolome analysis. Nature Methods, 12, 523-526, 2015) Software for pre-processing, including peak extraction, denoising, deconvolution, peak alignment, outputting 3D data matrix in CSV format (original data matrix). The extracted peak information is compared with the database, the MassBank, Respect, and GNPS (14951 records in total) are searched thoroughly. The three-dimensional matrix includes information such as sample information, retention time, mass-to-charge ratio, and mass spectral response intensity (peak area).

2.4. Result Analysis

The identification result is shown in Table 3 below.

TABLE 3

| Average Rt (min) | Average Mz | Metabolite name | Adduct ion name | Formula | 17_1 Peak area | 17_2 Peak area | 18_1 Peak area | 18_2 Peak area |
|---|---|---|---|---|---|---|---|---|
| 3.95 | 91.0415 | L-(+)-Lactic acid | [M + H]+ | $C_3H_6O_3$ | 117248 | 318900 | 901821 | 784056 |
| 0.64 | 96.0444 | 3-Hydroxypyridine | [M + H]+ | $C_5H_5NO$ | 1584749000 | 2847214000 | 3586359000 | 3193391000 |
| 4.67 | 96.0444 | 4-Hydroxypyridine | [M + H]+ | $C_5H_5NO$ | 119084 | 168545 | 56169490 | 292356 |
| 4.63 | 104.0303 | L-Serine | [M + H]+ | $C_3H_7NO_3$ | 802900 | 919164 | 214379500 | 187913000 |
| 0.58 | 104.0706 | N,N-Dimethylglycine | [M + H]+ | $C_4H_9NO_2$ | 1636803 | 2473024 | 5323344 | 3574752 |
| 0.58 | 104.107 | Choline | [M + H]+ | $C_5H_{14}NO$ | 133923800 | 268955700 | 400120200 | 361841000 |
| 0.55 | 106.0863 | Diethanolamine | [M + H]+ | $C_4H_{11}NO_2$ | 50282950 | 53085950 | 39812460 | 46188840 |
| 3.04 | 107.0491 | BENZALDEHYDE | [M + H]+ | $C_7H_6O$ | 73583780 | 84061230 | 129239000 | 139728000 |
| 9.95 | 109.0224 | 1,4-BENZOQUINONE | [M + H]+ | $C_6H_4O_2$ | 134427100 | 82574910 | 184523400 | 166872900 |
| 6.5 | 118.0862 | Glycine-Betaine | [M + H]+ | $C_5H_{11}NO_2$ | 64920350 | 92724650 | 206312 | 181607 |
| 0.21 | 118.1008 | Betaine | [M + H]+ | $C_5H_{11}NO_2$ | 99996610 | 103002800 | 52519310 | 0 |
| 3.03 | 122.0965 | N,N-DIMETHYLANILINE | [M + H]+ | $C_8H_{11}N$ | 190825400 | 300862 | 171205700 | 199777600 |
| 1.13 | 124.0394 | Isonicotinic acid | [M + H]+ | $C_6H_5NO_2$ | 785400800 | 804701100 | 1646895000 | 1647507000 |
| 1.18 | 125.043 | N,N-Dimethylsulfamide | [M + H]+ | $C_2H_8N_2O_2S$ | 1157741 | 391017 | 498944 | 251612700 |
| 2.22 | 129.0259 | 4-Amino-2-chloropyridine | [M + H]+ | $C_5H_5ClN_2$ | 137621 | 94660 | 331448 | 516212 |
| 5.26 | 130.0652 | Indole-3-carbinol | [M + H—H2O]+ | $C_9H_9NO$ | 141019800 | 214304700 | 99806730 | 94641380 |
| 2.43 | 130.0864 | 1-Amino-1-cyclopentanecarboxylic acid | [M + H]+ | $C_6H_{11}NO_2$ | 124622600 | 228075200 | 374911700 | 383800800 |
| 3.95 | 132.0805 | Creatine | [M + H]+ | $C_4H_9N_3O_2$ | 101699 | 235678 | 66433120 | 939623 |
| 2.32 | 136.0616 | Adenine | [M + H]+ | $C_5H_5N_5$ | 1410184 | 115325200 | 133190900 | 153512100 |
| 4.8 | 137.0467 | Allopurinol | [M + H]+ | $C_5H_4N_4O$ | 17254020 | 830011 | 40741750 | 37842160 |
| 2.3 | 138.0915 | Tyramine | [M + H]+ | $C_8H_{11}NO$ | 370477 | 255401700 | 252954100 | 272474200 |
| 1.43 | 140.0342 | 4-Nitrophenol | [M + H]+ | $C_6H_5NO_3$ | 1066120 | 635266 | 4148419 | 4349592 |
| 6.05 | 146.0601 | 3-Formylindole | [M + H]+ | $C_9H_7NO$ | 1858383000 | 2127830000 | 3809395000 | 3391581000 |
| 2.83 | 146.1178 | (S)-3-Amino-5-methylhexanoic acid | [M + H]+ | $C_7H_{15}NO_2$ | 71717160 | 83251700 | 355147600 | 362684600 |
| 4.54 | 147.044 | Coumarin | [M + H]+ | $C_9H_6O_2$ | 132517100 | 116201900 | 100971900 | 94392320 |
| 4.32 | 147.0553 | 1H-quinazolin-4-one | [M + H]+ | $C_8H_6N_2O$ | 348431800 | 550802900 | 724615600 | 673335000 |
| 9.25 | 149.0232 | Phthalic anhydride | [M + H]+ | $C_8H_4O_3$ | 3567044000 | 3010669000 | 466938200 | 801036200 |
| 0.64 | 150.1124 | Triethanolamine | [M + H]+ | $C_6H_{15}NO_3$ | 897905 | 789198 | 884032 | 597809 |
| 3.85 | 150.1279 | Methamphetamine | [M + H]+ | $C_{10}H_{15}N$ | 1471281 | 109738700 | 96871290 | 191582800 |
| 4.29 | 151.0467 | 4-hydroxy-1-methyl-2-oxopyridine-3-carbonitrile | [M + H]+ | $C_7H_6N_2O_2$ | 643358 | 684516 | 657822 | 325948 |
| 4.74 | 151.0859 | (S)-(+)-2-Phenylpropionic acid | [M + H]+ | $C_9H_{10}O_2$ | 82923 | 137149700 | 323506 | 92544050 |

TABLE 3-continued

| Average Rt (min) | Average Mz | Metabolite name | Adduct ion name | Formula | 17_1 Peak area | 17_2 Peak area | 18_1 Peak area | 18_2 Peak area |
|---|---|---|---|---|---|---|---|---|
| 4 | 152.0545 | Guanine | [M + H]+ | $C_5H_5N_5O$ | 272580 | 302846 | 194968 | 310477 |
| 2.63 | 152.0709 | Phenylglycine | [M + H]+ | $C_8H_9NO_2$ | 1927128 | 1263779 | 4696618 | 4399683 |
| 3.02 | 156.0655 | N-(2,5-dioxocyclopentyl)acetamide | [M + H]+ | $C_7H_9NO_3$ | 186490 | 227727 | 188238 | 204802 |
| 7 | 156.0676 | Indole-3-acetonitrile | [M + H]+ | $C_{10}H_8N_2$ | 72747800 | 29234050 | 548241 | 317970 |
| 2.8 | 160.097 | N-Isovaleroylglycine | [M + H]+ | $C_7H_{13}NO_3$ | 543275 | 37301430 | 248658000 | 205351800 |
| 2.64 | 161.0709 | 1H-indole-3-carboxamide | [M + H]+ | $C_9H_8N_2O$ | 10778720 | 121616300 | 8466366 | 8066009 |
| 5.95 | 162.0467 | 1H-indole-3-carboxylic acid | [M + H]+ | $C_9H_7NO_2$ | 191799700 | 93008490 | 287471400 | 257985900 |
| 4.47 | 163.0392 | 7-hydroxy-coumarin | [M + H]+ | $C_9H_6O_3$ | 478075 | 63672860 | 79780530 | 80264080 |
| 4.64 | 163.0574 | 1,6-Anhydro-beta-D-glucose | [M + H]+ | $C_6H_{10}O_5$ | 372356 | 423056 | 36000160 | 539394 |
| 2.21 | 164.0794 | R-3-Amino-5-(methylthio)pentanoic acid | [M + H]+ | $C_6H_{13}NO_2S$ | 25705920 | 37612020 | 37459400 | 47617300 |
| 2.91 | 165.0581 | trans-p-Hydroxycinnamic acid | [M + H]+ | $C_9H_8O_3$ | 356840800 | 241868800 | 348058400 | 331919700 |
| 4.62 | 170.0967 | Diphenylamine | [M + H]+ | $C_{12}H_{11}N$ | 119687 | 135413 | 169306 | 60571 |
| 4.03 | 171.0653 | Propylthiouracil | [M + H]+ | $C_7H_{10}N_2OS$ | 108857600 | 230898800 | 164634800 | 179944700 |
| 0.46 | 174.0248 | Sulfanilic acid | [M + H]+ | $C_6H_7NO_3S$ | 26811580 | 33826000 | 700360 | 35428540 |
| 2.01 | 175.028 | cis-Aconitate | [M + H]+ | $C_6H_6O_6$ | 749634800 | 3026028000 | 424597000 | 251250100 |
| 8.34 | 176.071 | Indoleacetic acid | [M + H]+ | $C_{10}H_9NO_2$ | 1371392 | 609474 | 644521 | 394001 |
| 4.27 | 177.0497 | N-Carbamoyl-L-Aspartic acid | [M + H]+ | $C_5H_8N_2O_5$ | 20399620 | 50335850 | 315011 | 277598 |
| 4.25 | 179.034 | 6,7-DIHYDROXYCOUMARIN | [M + H]+ | $C_9H_6O_4$ | 243406000 | 81711660 | 538391600 | 560991000 |
| 8.01 | 180.0654 | N-BENZOYL(D5)GLYCINE | [M + H]+ | $C_9H_9NO_3$ | 3874055 | 1466982 | 1300229 | 821451 |
| 2.69 | 182.0528 | L-Methionine sulfone | [M + H]2+ | $C_5H_{11}NO_4S$ | 543834 | 148525300 | 107604000 | 110868600 |
| 4.26 | 191.0471 | 8-HYDROXY-5-NITROQUINOLINE | [M + H]+ | $C_9H_6N_2O_3$ | 223770200 | 518971 | 205955400 | 221812600 |
| 4.8 | 192.0653 | 5-Hydroxyindole-3-acetic acid | [M + H]+ | $C_{10}H_9NO_3$ | 77190250 | 242664000 | 190467500 | 164613300 |
| 5.55 | 193.0496 | Scopoletin | [M + H]+ | $C_{10}H_8O_4$ | 112951300 | 132978700 | 107398000 | 116233400 |
| 7.32 | 193.0754 | Quinic acid | [M + H]+ | $C_7H_{12}O_6$ | 138071100 | 162858000 | 136003600 | 148700700 |
| 8.1 | 194.1177 | N,N-Diethyl-4-hydroxybenzamide | [M + H]+ | $C_{11}H_{15}NO_2$ | 161763 | 156407 | 215583 | 167671 |
| 4.03 | 195.0879 | Caffeine | [M + H]+ | $C_8H_{10}N_4O_2$ | 281324300 | 1260529000 | 120808800 | 116743000 |
| 3.94 | 197.0598 | 1,3-Dimethylurate | [M + H]+ | $C_7H_8N_4O_3$ | 31561 | 100517 | 515771 | 649587 |
| 7.69 | 198.0963 | Galactose | [M + H]+ | $C_6H_{12}O_6$ | 27053410 | 26161900 | 782902 | 24387520 |
| 10.82 | 209.0888 | Kynurenine | [M + H]+ | $C_{10}H_{12}N_2O_3$ | 6500341 | 4171507000 | 1605694 | 916243 |
| 5.63 | 209.1285 | Pilocarpine | [M + H]+ | $C_{11}H_{16}N_2O_2$ | 322564400 | 612663800 | 764132700 | 665717200 |
| 4.97 | 213.1023 | HARMINE | [M + H]+ | $C_{13}H_{12}N_2O$ | 829288300 | 765980100 | 764976300 | 687628500 |
| 5.16 | 215.1392 | d-Desthiobiotin | [M + H]+ | $C_{10}H_{18}N_2O_3$ | 4767149 | 29536420 | 42187360 | 37513320 |
| 7.49 | 222.1019 | N-Acetyl-D-mannosamine | [M + H]+ | $C_8H_{15}NO_6$ | 129143000 | 255760600 | 334410000 | 333452300 |
| 4.49 | 224.128 | Bufexamac | [M + H]+ | $C_{12}H_{17}NO_3$ | 138720 | 145423 | 269514 | 316777 |
| 2.26 | 226.1076 | 6-Benzyladenine | [M + H]+ | $C_{12}H_{11}N_5$ | 233398 | 10068140 | 17556700 | 19329320 |
| 4.58 | 230.0811 | 6-Demethoxy-isomaculosidine | [M + H]+ | $C_{13}H_{11}NO_3$ | 33811620 | 66093560 | 51267740 | 49992810 |
| 2.21 | 245.077 | Uridine | [M + H]+ | $C_9H_{12}N_2O_6$ | 16696020 | 13484340 | 37297080 | 37326080 |
| 2.34 | 252.1093 | 2'-Deoxyadenosine | [M + H]+ | $C_{10}H_{13}N_5O_3$ | 49797100 | 362137200 | 207804800 | 207364600 |
| 5.21 | 261.0399 | D-Mannose-6-phosphate | [M + H]+ | $C_6H_{13}O_9P$ | 171840 | 0 | 0 | 45978 |
| 0.65 | 268.1038 | Adenosine | [M + H]+ | $C_{10}H_{13}N_5O_4$ | 266029700 | 484828200 | 820300800 | 895448400 |
| 8.35 | 318.3003 | Phytosphingosine | [M + H]+ | $C_{18}H_{39}NO_3$ | 8398809000 | 12589620000 | 5946451000 | 5953316000 |
| 7.61 | 327.207 | Hydroquinine | [M + H]+ | $C_{20}H_{26}N_2O_2$ | 21543470 | 71029540 | 31195720 | 28285790 |
| 8.81 | 383.076 | Rosmarinic acid | [M + H]+ | $C_{18}H_{16}O_8$ | 5270792000 | 5361477000 | 5681337000 | 4946908000 |
| 9.25 | 440.2783 | 1-Lauroyl-2-hydroxy-sn-glycero-3-phosphocholine | [M + H]+ | $C_{20}H_{42}NO_7P$ | 69427400 | 189091 | 261524 | 215915 |
| 10.55 | 89.0242 | Lactic acid | [M − H]− | $C_3H_6O_3$ | 612071900 | 456634 | 901353 | 1875008 |
| 3.95 | 103.0399 | 2-METHYLLACTIC ACID | [M − H]− | $C_4H_8O_3$ | 38066 | 29287 | 112521 | 96549 |
| 0.65 | 105.0191 | Glyceric acid | [M − H]− | $C_3H_6O_4$ | 24745640 | 27781010 | 40970310 | 36504630 |
| 3.09 | 109.0291 | Catechol | [M − H]− | $C_6H_6O_2$ | 2247239 | 98470 | 6754215 | 8211577 |
| 1.27 | 115.0057 | MALEIC ACID | [M − H]− | $C_4H_4O_4$ | 145741 | 49513000 | 28231080 | 26311120 |
| 10.22 | 117.0191 | Succinic acid | [M − H]− | $C_4H_6O_4$ | 53176200 | 114106 | 48594 | 148112 |
| 3.13 | 117.0555 | 3-Hydroxyisovaleric acid | [M − H]− | $C_5H_{10}O_3$ | 557058900 | 1252103000 | 1178460000 | 1109623000 |
| 2.97 | 128.035 | L-5-Oxoproline | [M − H]− | $C_5H_7NO_3$ | 3886901 | 4496670 | 11026300 | 10077880 |
| 4.8 | 129.0555 | Ketoisoleucine | [M − H]− | $C_6H_{10}O_3$ | 94561 | 86435 | 117561 | 102127 |
| 0.65 | 134.047 | Adenine | [M − H]− | $C_5H_5N_5$ | 61311660 | 16580950 | 23945600 | 22623320 |
| 3.72 | 137.0242 | Salicylic acid | [M − H]− | $C_7H_6O_3$ | 633172700 | 598075900 | 1421922000 | 1366332000 |
| 3.18 | 144.0452 | 3-FORMYLINDOLE | [M − H]− | $C_9H_7NO$ | 62867 | 93514 | 37758660 | 27126110 |
| 6.06 | 144.0452 | Indole-3-carboxaldehyde | [M − H]− | $C_9H_7NO$ | 705596000 | 775093200 | 1185595000 | 1081837000 |
| 2.38 | 145.0503 | 2-Methylglutaric acid | [M − H]− | $C_6H_{10}O_4$ | 245812300 | 384215600 | 997858800 | 838499200 |
| 1.24 | 147.0296 | Citramalate | [M − H]− | $C_5H_8O_5$ | 132996 | 314902 | 156690 | 115459 |
| 5.23 | 147.0449 | trans-Cinnamate | [M − H]− | $C_9H_8O_2$ | 8168007 | 6975507 | 40011630 | 27263440 |
| 2.1 | 151.0257 | Oxypurinol | [M − H]− | $C_5H_4N_4O_2$ | 101514 | 56409790 | 61413950 | 72074230 |
| 5.55 | 151.0398 | MANDELIC ACID | [M − H]− | $C_8H_8O_3$ | 100825500 | 247188200 | 159204600 | 149263600 |
| 4.83 | 151.0398 | 2-Hydroxyphenylacetic acid | [M − H]− | $C_8H_8O_3$ | 2742320000 | 1152762000 | 2799137000 | 2418272000 |
| 4.18 | 151.0398 | Vanillin | [M − H]− | $C_8H_8O_3$ | 641381800 | 1249361000 | 1284858000 | 1226022000 |
| 0.61 | 151.0609 | Adonitol | [M − H]− | $C_5H_{12}O_5$ | 631196 | 36442650 | 59498680 | 53897530 |

TABLE 3-continued

| Average Rt (min) | Average Mz | Metabolite name | Adduct ion name | Formula | 17_1 Peak area | 17_2 Peak area | 18_1 Peak area | 18_2 Peak area |
|---|---|---|---|---|---|---|---|---|
| 3.09 | 153.0191 | 3,4-DIHYDROXYBENZOIC ACID | [M − H]− | $C_7H_6O_4$ | 227879500 | 158822300 | 567161400 | 507212400 |
| 3.87 | 153.0191 | 2,5-DIHYDROXYBENZOIC ACID | [M − H]− | $C_7H_6O_4$ | 92391780 | 69517170 | 339520200 | 300232900 |
| 4.97 | 153.0555 | 4-hidroxy-3-methoxybenzyl alcohol | [M − H]− | $C_8H_{10}O_3$ | 51120460 | 65147150 | 75533580 | 71754540 |
| 3.34 | 154.0508 | N-(2,5-dioxocyclopentyl)acetamide | [M − H]− | $C_7H_9NO_3$ | 11892270 | 22063550 | 30937010 | 28926530 |
| 3.48 | 158.0818 | N-Isovaleroylglycine | [M − H]− | $C_7H_{13}NO_3$ | 8113735 | 7132749 | 41309960 | 39603790 |
| 4.85 | 159.0658 | PIMELIC ACID | [M − H]− | $C_7H_{12}O_4$ | 113443 | 110003 | 15804010 | 15409650 |
| 4.48 | 162.0557 | L-beta-Homomethionine | [M − H]− | $C_6H_{13}NO_2S$ | 166192100 | 350440600 | 380748300 | 342105600 |
| 5.19 | 163.04 | trans-p-Hydroxycinnamic acid | [M − H]− | $C_9H_8O_3$ | 356740 | 51884990 | 83639580 | 68269900 |
| 3.13 | 163.0608 | 2-Deoxy-D-glucose | [M − H]− | $C_6H_{12}O_5$ | 74329 | 19842430 | 15519390 | 13103480 |
| 4.34 | 166.0508 | Pyridoxal | [M − H]− | $C_8H_9NO_3$ | 212089 | 26063020 | 32484040 | 29011410 |
| 4.41 | 167.0345 | 3-Hydroxymandelic acid | [M − H]− | $C_8H_8O_4$ | 1599787 | 1956448 | 186696400 | 171364500 |
| 3.36 | 167.0345 | 3,4-Dihydroxyphenylacetic acid | [M − H]− | $C_8H_8O_4$ | 173067800 | 1327129 | 283878300 | 275640400 |
| 4.73 | 167.0346 | Homogentisic acid | [M − H]− | $C_8H_8O_4$ | 92002270 | 660452 | 181348500 | 168103300 |
| 3.19 | 173.0088 | cis-Aconitate | [M − H]− | $C_6H_6O_6$ | 0 | 0 | 9091 | 0 |
| 2.65 | 173.0451 | (−)-Shikimic acid | [M − H]− | $C_7H_{10}O_5$ | 22119660 | 36416400 | 79466300 | 70365200 |
| 5.26 | 173.0818 | SUBERIC ACID | [M − H]− | $C_8H_{14}O_4$ | 259058700 | 203833600 | 563239000 | 493673600 |
| 8.34 | 174.0557 | BETA-INDOLEACETIC ACID | [M − H]− | $C_{10}H_9NO_2$ | 19730570 | 8680877 | 3719550 | 4292181 |
| 6.92 | 175.0397 | 4-Methylumbelliferone | [M − H]− | $C_{10}H_8O_3$ | 6373958 | 5960572 | 7489743 | 6462846 |
| 3.74 | 175.0608 | 2-Isopropylmalic acid | [M − H]− | $C_7H_{12}O_5$ | 52374880 | 7745416 | 1704333000 | 260786800 |
| 4.76 | 177.0191 | Daphnetin | [M − H]− | $C_9H_6O_4$ | 194961 | 124993 | 771682 | 609157 |
| 4.27 | 177.0191 | 6,7-DIHYDROXYCOUMARIN | [M − H]− | $C_9H_6O_4$ | 1835262000 | 513843600 | 2739756000 | 2562066000 |
| 4.8 | 178.0867 | L-beta-Homophenylalanine | [M − H]− | $C_{10}H_{13}NO_2$ | 19252 | 15125 | 0 | 0 |
| 4.34 | 179.0346 | CAFFEIC ACID | [M − H]− | $C_9H_8O_4$ | 187408900 | 154434100 | 542478900 | 534266200 |
| 4.36 | 180.066 | Tyr | [M − H]− | $C_9H_{11}NO_3$ | 285797 | 25213730 | 678328 | 770202 |
| 5.96 | 182.9881 | Carbamimidothioic acid | [M − H]− | $C_3H_8N_2O_3S_2$ | 24872 | 50236 | 57144 | 18363 |
| 6.8 | 186.1134 | 3-(2-amino-2-oxoethyl)-5-methyl-hexanoic acid | [M − H]− | $C_9H_{17}NO_3$ | 830907 | 2005731 | 5597838 | 5071310 |
| 5.59 | 188.0349 | Kynurenic acid | [M − H]− | $C_{10}H_7NO_3$ | 21580670 | 16285910 | 167225200 | 145805900 |
| 5.55 | 191.0346 | Scopoletin | [M − H]− | $C_{10}H_8O_4$ | 82219140 | 55976820 | 62875630 | 60615110 |
| 2.35 | 191.0558 | Quinic acid | [M − H]− | $C_7H_{12}O_6$ | 60683 | 72527 | 123264 | 66878 |
| 5.13 | 192.0663 | PHENATURIC ACID | [M − H]− | $C_{10}H_{11}NO_3$ | 8520897 | 235446 | 51849750 | 52247300 |
| 0.66 | 193.035 | D-(+)-Galacturonic acid | [M − H]− | $C_6H_{10}O_7$ | 31829000 | 53619800 | 50122970 | 62835640 |
| 4.64 | 193.05 | 3-(4-HYDROXY-3-METHOXYPHENYL)PROP-2-ENOICACID | [M − H]− | $C_{10}H_{10}O_4$ | 57151 | 143421 | 197296 | 205592 |
| 5.49 | 196.0611 | DOPA | [M − H]− | $C_9H_{11}NO_4$ | 108303 | 7515738 | 342328 | 13181440 |
| 5.15 | 197.0451 | Syringate | [M − H]− | $C_9H_{10}O_5$ | 132261600 | 379039900 | 188873800 | 176294000 |
| 7.45 | 201.1131 | Sebacate | [M − H]− | $C_{10}H_{18}O_4$ | 158851900 | 110601200 | 188788800 | 177044500 |
| 7.68 | 207.0659 | Sinapyl aldehyde | [M − H]− | $C_{11}H_{12}O_4$ | 108136100 | 49228680 | 145318700 | 145826400 |
| 6.79 | 209.0244 | Mucate | [M − H]− | $C_6H_{10}O_8$ | 24879850 | 18134340 | 12288540 | 14426330 |
| 6.65 | 211.061 | 2,4,5-trimethoxybenzoic acid | [M − H]− | $C_{10}H_{12}O_5$ | 2596152 | 14111230 | 97512 | 116431 |
| 2.86 | 218.1033 | Pantothenate | [M − H]− | $C_9H_{17}NO_5$ | 10037510 | 1907950 | 24315530 | 23535220 |
| 8.29 | 223.1335 | Methyl Jasmonate | [M − H]− | $C_{13}H_{20}O_3$ | 48671080 | 18173640 | 184152700 | 170601200 |
| 8.7 | 225.1492 | METHYL DIHYDROJASMONATE | [M − H]− | $C_{13}H_{22}O_3$ | 344722 | 43871220 | 45862210 | 585955 |
| 6.84 | 226.0871 | 2'-Deoxycytidine | [M − H]− | $C_9H_{13}N_3O_4$ | 6461148 | 10017050 | 7241176 | 5580852 |
| 8.44 | 227.0713 | Resveratrol | [M − H]− | $C_{14}H_{12}O_3$ | 2999943 | 13394450 | 43642440 | 38246730 |
| 2.69 | 241.083 | Thymidine | [M − H]− | $C_{10}H_{14}N_2O_5$ | 2740873 | 10856050 | 9701001 | 7751767 |
| 8.31 | 242.0821 | Cytidine | [M − H]− | $C_9H_{13}N_3O_5$ | 80463300 | 77348980 | 128604300 | 121548800 |
| 2.21 | 243.0621 | Uridine | [M − H]− | $C_9H_{12}N_2O_6$ | 10120340 | 25719180 | 32539360 | 25112650 |
| 2.46 | 244.9975 | gamma,gamma-Dimethyallyl pyrophosphate ammonium salt | [M − H]− | $C_5H_{12}O_7P_2$ | 3110806 | 137893 | 247673 | 198908 |
| 5 | 259.0242 | Mannose 6-phosphate | [M − H]− | $C_6H_{13}O_9P$ | 5531674 | 18431 | 98232 | 85938 |
| 7.32 | 263.1283 | (+/−)-cis,trans-abscisic acid | [M − H]− | $C_{15}H_{20}O_4$ | 98303270 | 146908700 | 146636400 | 142106400 |
| 4.06 | 271.0786 | Naringenin | [M − H]− | $C_{15}H_{12}O_5$ | 698930 | 1063414 | 5402730 | 4700528 |
| 5.44 | 275.0195 | 6-Phosphogluconate | [M − H]− | $C_6H_{13}O_{10}P$ | 15145 | 0 | 24429 | 18951 |
| 8.33 | 275.1289 | L-Saccharopine | [M − H]− | $C_{11}H_{20}N_2O_6$ | 58251290 | 94510280 | 55271610 | 42867540 |
| 9.15 | 279.16 | 2-(8-hydroxyoctyl)-6-methoxybenzoic acid | [M − H]− | $C_{16}H_{24}O_4$ | 126522500 | 201502400 | 84745540 | 102741000 |
| 8.74 | 279.2325 | Linoleic acid | [M − H]− | $C_{18}H_{32}O_2$ | 54552 | 49023570 | 39206830 | 37163050 |
| 4.57 | 282.0768 | Guanosine | [M − H]− | $C_{10}H_{13}N_5O_5$ | 890809 | 2104308 | 4094789 | 2495333 |
| 8.76 | 285.0405 | Kaempferol | [M − H]− | $C_{15}H_{10}O_6$ | 33811620 | 2032376 | 3394481 | 3204039 |
| 7.91 | 289.0685 | Catechin | [M − H]− | $C_{15}H_{14}O_6$ | 45759 | 16436200 | 502525 | 13512580 |
| 8.97 | 295.2278 | 12,13-EODE | [M − H]− | $C_{18}H_{32}O_3$ | 749766800 | 616195700 | 273151000 | 274151900 |
| 7.65 | 301.0355 | Quercetin | [M − H]− | $C_{15}H_{10}O_7$ | 39084910 | 31996040 | 55956030 | 14881350 |
| 9.42 | 301.0752 | Homoeriodictyol | [M − H]− | $C_{16}H_{14}O_6$ | 29075 | 74551710 | 13787760 | 19162120 |
| 3.71 | 303.0507 | Taxifolin | [M − H]− | $C_{15}H_{12}O_7$ | 11019570 | 15614380 | 28203220 | 24560380 |

TABLE 3-continued

| Average Rt (min) | Average Mz | Metabolite name | Adduct ion name | Formula | 17_1 Peak area | 17_2 Peak area | 18_1 Peak area | 18_2 Peak area |
|---|---|---|---|---|---|---|---|---|
| 5.78 | 309.0611 | Sulfadimethoxine | [M − H]− | $C_{12}H_{14}N_4O_4S$ | 5002510 | 88714 | 28127620 | 23156070 |
| 9.01 | 311.2225 | 13-HPODE | [M − H]− | $C_{18}H_{32}O_4$ | 555426 | 301702 | 152443 | 252579 |
| 8.69 | 311.2225 | Methyl-13-hydroperoxy-delta9E,11E-octadecadienoic acid | [M − H]− | $C_{19}H_{34}O_4$ | 538841800 | 507996400 | 194171300 | 181638700 |
| 9.57 | 315.0874 | Eriodictyol 7,3'-dimethyl ether | [M − H]− | $C_{17}H_{16}O_6$ | 2138308 | 88879740 | 31636900 | 26793380 |
| 9.64 | 319.1213 | Mycophenolic acid | [M − H]− | $C_{17}H_{20}O_6$ | 147188 | 59991020 | 37473510 | 31707840 |
| 7.78 | 329.1398 | Gibberellin A5 | [M − H]− | $C_{19}H_{22}O_5$ | 449998 | 26397890 | 33367390 | 766327 |
| 7.89 | 330.055 | 2'-Deoxyadenosine 5'-monophosphate | [M − H]− | $C_{10}H_{14}N_5O_6P$ | 2511490 | 9987048 | 7330539 | 10790330 |
| 8.69 | 333.2069 | LTB5 | [M − H]− | $C_{20}H_{30}O_4$ | 9670628 | 959944300 | 23376100 | 24098480 |
| 9.84 | 343.1207 | Maltitol | [M − H]− | $C_{12}H_{24}O_{11}$ | 226245 | 75487880 | 5064388 | 188036 |
| 5.49 | 345.1341 | Gibberellic acid | [M − H]− | $C_{19}H_{22}O_6$ | 22516490 | 66624980 | 95575120 | 91717860 |
| 8.64 | 347.1867 | Gibberellin A53 | [M − H]− | $C_{20}H_{28}O_5$ | 600058600 | 719294300 | 1737611000 | 1493233000 |
| 8.47 | 349.2021 | 8-(3-((1-ethoxy-2-methyl-1-oxopropan-2-yl)oxy)phenyl)octanoic acid | [M − H]− | $C_{20}H_{30}O_5$ | 126346900 | 83072170 | 147630700 | 147971800 |
| 9.32 | 351.2177 | LTB4_20-Hydroxy | [M − H]− | $C_{20}H_{32}O_5$ | 18323610 | 122153300 | 34749160 | 60868540 |
| 3.95 | 353.0875 | 3-Caffeoylquinic acid | [M − H]− | $C_{16}H_{18}O_9$ | 1173515 | 50569490 | 5472397 | 4990544 |
| 9.83 | 353.1423 | Xanthohumol | [M − H]− | $C_{21}H_{22}O_5$ | 12744510 | 178726 | 129917 | 73077 |
| 4.32 | 359.0777 | Rosmarinic acid | [M − H]− | $C_{18}H_{16}O_8$ | 66493 | 1417658 | 5285221 | 5317162 |
| 7.48 | 361.1651 | Gibberellin A19 | [M − H]− | $C_{20}H_{26}O_6$ | 5632593 | 196296 | 166138 | 241419 |
| 5.24 | 367.1029 | 5-O-Caffeoylquinic acid methyl ester | [M − H]− | $C_{17}H_{20}O_9$ | 39303 | 16827540 | 65734 | 25636 |
| 5.26 | 385.1176 | 1-O-b-D-glucopyranosyl sinapate | [M − H]− | $C_{17}H_{22}O_{10}$ | 5784527 | 3487297 | 20396460 | 16538220 |
| 7.25 | 461.1132 | Peonidine-3-O-glucoside chloride | [M − H]− | $C_{22}H_{23}O_{11}$ | 20482520 | 41647460 | 24178540 | 24364040 |
| 5.92 | 515.1189 | 3,5-Dicaffeoylquininic acid | [M − H]− | $C_{25}H_{24}O_{12}$ | 0 | 9151134 | 17143 | 0 |
| 9.59 | 831.5031 | Phosphatidylinositol | [M − H]− | $C_{43}H_{77}O_{13}P$ | 338967 | 118224700 | 598568 | 342103 |

The substances identified by LC-MS are shown in Table 3 above, including reported main active components (meaning the substances represented by the peaks with a peak area above $10^5$) investigated by the present inventors. 17# includes: betaine, scopoletin, harmine, rosmarinic acid, oxipurinol, resveratrol, naringenin, kaempferol, catechin, taxifolin, and xanthohumol. 18# includes: scopoletin, harmine, rosmarinic acid, oxipurinol, resveratrol, naringenin, kaempferol, catechin, taxifolin, and xanthohumol.

Since only the currently known compounds can be detected by LC-MC, the results of this LC-MC analysis has indicated some components with anti-tumor and anti-bacterial activity, and it is still necessary to carry out further study to find whether unknown active compounds are contained in the fermentation broth.

Example 10. In Vitro Antibacterial Activity Study

1. Experimental Steps

The strain to be tested was inoculated into an Erlenmeyer flask containing 100 ml of LB liquid medium, and cultured at 37° C. for 10 to 12 hours in a shaker at 120 r/min. 100 ml LB solid medium was prepared, sterilized and cooled to an appropriate temperature. The bacterial suspension to be tested was added (where typically, 100 microliters of bacterial suspension was added per 100 ml solid medium) on an ultra-clean workbench, shaken until uniform, transferred to a plate, and stood to solidify. The back of the plate after solidification was divided generally into three to four areas, and the samples added in each area were marked. An oxford cup was placed firmly preferably in the center of each area, and pressed gently, while guaranteeing that the cup cannot be inserted into the plate. After being placed, 100 to 200 microliters of a sample (where the sample is the metabolite product 17 # of a gingko-derived endophytic fungus, or the metabolite product 18 # of a gingko-derived endophytic fungus obtained in Example 6) was added to each cup. The plate was stably placed in an incubator at 37° C., and the results were observed after 9 to 12 hours.

Note: In this disclosure, a variety of gingko-derived endophytic fungi were tested, and numbered. Relatively good test results are presented in this disclosure, where 17 # and 18 # are J-1 and J-2, respectively, and Strain 17# is gingko-derived endophytic fungus *Fusarium proliferatum* DZHQ1, deposited under the CGMCC Accession No. 14983.

2. Test Results:

2.1. Inhibitory Effect on *E. coli*

Figure 10:
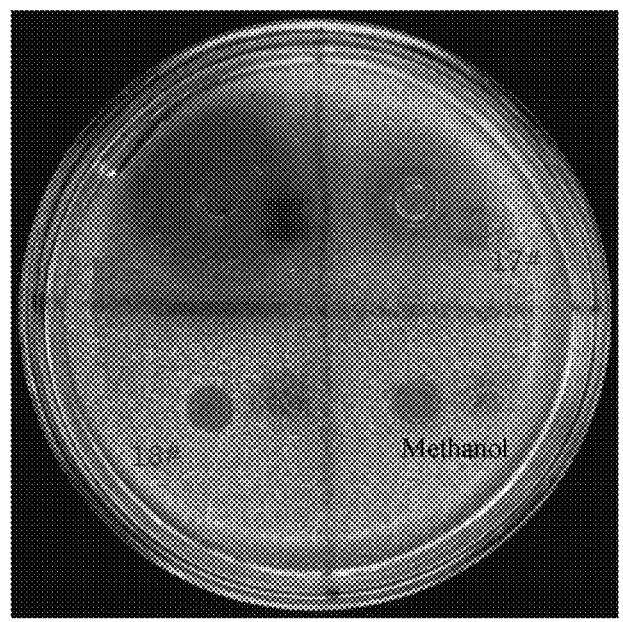
FIG. 10 shows the inhibitory effects of solutions of the extracts $17^\#$ and $18^\#$ of the gingko-derived endophytic fungi in methanol on *E. coli*.

FIG. 10 shows the test results for the inhibitory effects of solutions of the crude extracts 17# and 18# of gingko-derived endophytic fungi in methanol obtained in Example 6 and methanol on *E. coli*. 17# represents a solution of the crude extract 17# of a gingko-derived endophytic fungus in methanol; 18# represents a solution of the crude extract 18# of a gingko-derived endophytic fungus in methanol; and "methanol" represents a methanol solution. As can be seen from the figure, the gingko-derived endophytic fungus 17# has an inhibitory zone with a diameter of 0.9 cm. The inhibitory effects of the gingko-derived endophytic fungus 18# and the methanol solution is weak, and scarcely present.

Figure 11:
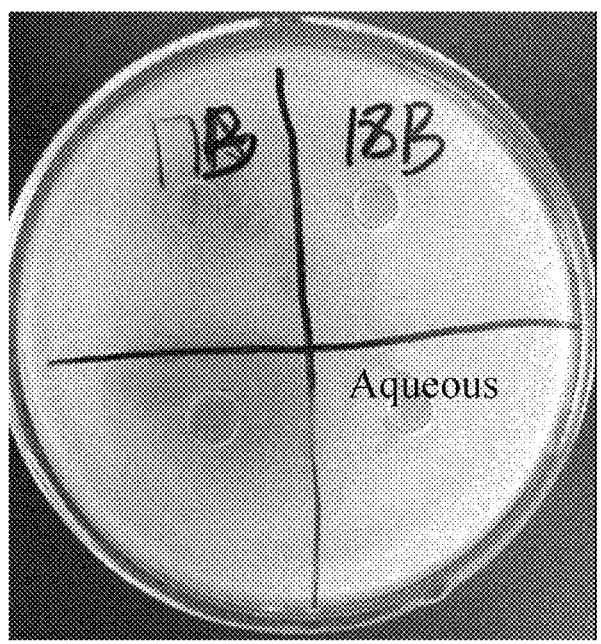
FIG. 11 shows the inhibitory effects of solutions of the extracts $17^\#$ and $18^\#$ of the gingko-derived endophytic fungi in water on *E. coli*.

FIG. 11 shows the inhibitory effects of solutions of the crude extracts of the gingko-derived endophytic fungi in water obtained in Example 6 on *E. coli*. 17#B represents the solution of the crude extract of gingko-derived endophytic fungus 17# in water; 18#B represents the solution of the crude extract of gingko-derived endophytic fungus 18# in water; and "aqueous" represents an aqueous solution. As can be seen from the figure, they both have no antibacterial effect.

In summary, for the gingko-derived endophytic fungi 17# and 18#, the endophytic fungus 17# has an obviously inhibition on *E. coli*, and the inhibitory effect of the endophytic fungus 18# is non-obvious, and is almost 0. In addition, it can also be seen from this experiment that the metabolites extracted with different solvents have different inhibitory effects on *E. coli*. The methanol solution of the crude extract 17# has a more notable inhibitory effect on *E. coli*.

2.2. Inhibitory Effect on *S. aureus*

The sample 17# or 18# obtained in Example 6 was used in the Oxford cup antibacterial test. The result is shown below.

Figure 12:
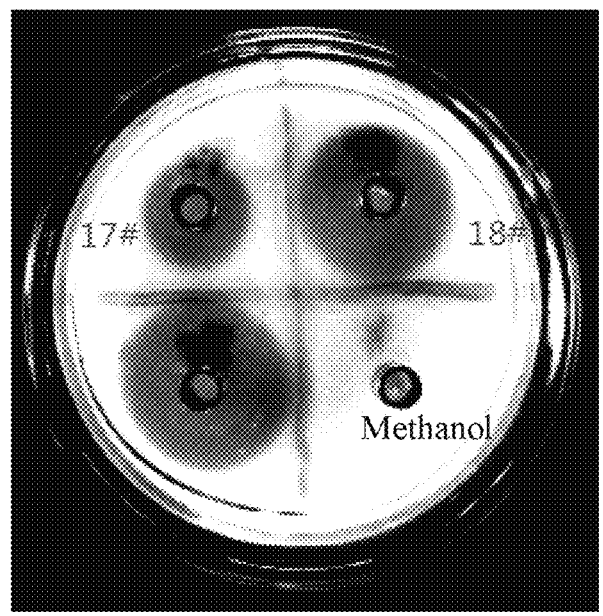
FIG. 12 shows the inhibitory effects of solutions of the extracts $17^\#$ and $18^\#$ of the gingko-derived endophytic fungi in methanol on *S. aureus*.

FIG. 12 shows the inhibitory effects of solutions of the extracts of gingko-derived endophytic fungi in methanol obtained in Example 6 on *S. aureus*. As shown by the experimental results, 17# and 18# have a certain inhibitory effect, and the diameter of the inhibition zone is 2 cm and 2.9 cm, respectively.

Figure 13:
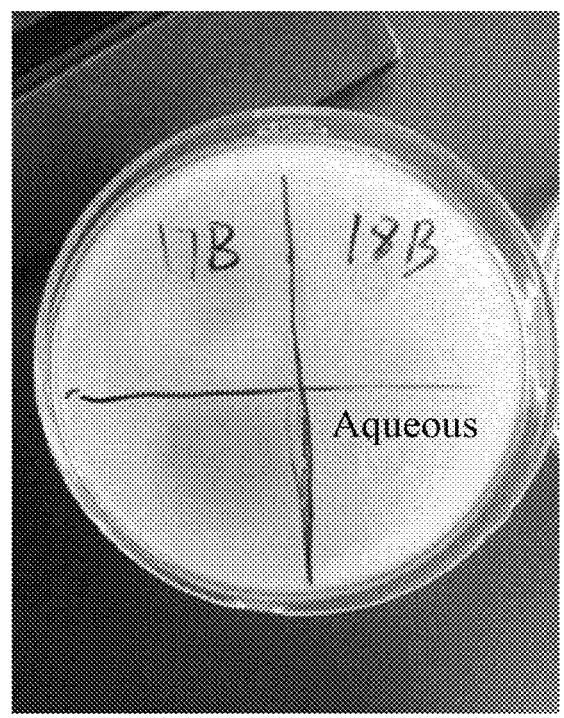
FIG. 13 shows the inhibitory effects of solutions of the extracts $17^\#$ and $18^\#$ of the gingko-derived endophytic fungi in water on *S. aureus*.

FIG. 13 shows the inhibitory effects of solutions of the extracts of the gingko-derived endophytic fungi in water obtained in Example 6 on *S. aureus*. As can be observed, although some inhibition zones are not very clear, the metabolite of the endophytic fungus 17# has a certain antibacterial activity, and the inhibitory effect of the gingko-derived endophytic fungus 18# and is weak, and scarcely present.

The results show that the gingko-derived endophytic fungi 17# and 18# have an inhibitory effect on *S. aureus*. It can also be seen from this experiment that the metabolites extracted with different solvents have different inhibitory effects on *S. aureus*. The solutions of the crude extract 17# in methanol and water have obvious inhibitory effects on *S. aureus*.

The above examples are preferred embodiments of the present invention, but the embodiments of the present invention are not limited to thereto. Any other changes, modifications, replacements, combinations, and simplifications may be made without departing from the spirit and scope of the present invention, which are all embraced in the scope of the present invention.

What is claimed is:

1. A method of obtaining a metabolite product, comprising:
   culturing an endophytic fungus from gingko on a Potato Dextrose Agar (PDA) solid medium;
   obtaining mycelial pellets of the endophytic fungus from the PDA solid medium;
   inoculating the mycelial pellets in a PDA liquid medium;
   culturing the endophytic fungus in the PDA liquid medium for 5-8 days at 20-28° C. to produce a fermentation broth comprising betaine, scopoletin, harmine, rosmarinic acid, oxipurinol, resveratrol, naringenin, catechin, taxifolin, and xanthohumol;
   adding ethyl acetate to the fermentation broth;
   culturing the endophytic fungus for another 4-8 days;
   filtering the fermentation broth to remove mycelium;
   obtaining an organic phase containing secondary metabolites of the endophytic fungus;
   recovering ethyl acetate from the organic phase to obtain a concentrate containing the secondary metabolites of the endophytic fungus;
   drying the concentrate to obtain an ethyl acetate extract of the fermentation broth; and
   dissolving the ethyl acetate extract of the fermentation broth in methanol to obtain the metabolite product of the endophytic fungus,
   wherein the endophytic fungus is *Fusarium proliferatum* DZHQ1, which was deposited in China General Microbiological Culture Collection Center (CGMCC) under the CGMCC Accession No. 14983 on Nov. 28, 2017.

2. The method of claim 1, wherein the endophytic fungus is cultured in the PDA liquid medium for 5-7 days in a shaker at 100-150 r/min.

3. The method of claim 1, wherein the ethyl acetate is added to the fermentation broth at a volume ratio of 1:1-2:1.

4. The method of claim 1, wherein the ethyl acetate extract of the fermentation broth comprises betaine, scopoletin, harmine, rosmarinic acid, oxipurinol, resveratrol, naringenin, catechin, taxifolin, and xanthohumol.

5. The method of claim 1, wherein the metabolite product comprises betaine, scopoletin, harmine, rosmarinic acid, oxipurinol, resveratrol, naringenin, catechin, taxifolin, and xanthohumol.

6. The method of claim 5, wherein the betaine, scopoletin, harmine, rosmarinic acid, oxipurinol, resveratrol, naringenin, catechin, taxifolin, and xanthohumol are represented by peaks having a peak area of $10^5$ or higher in an HPLC chromatogram.

7. The method of claim 1, wherein a ratio of the ethyl acetate extract to methanol is 0.01-0.05 g:1 mL.

8. The method of claim 1, further comprising
   combining the metabolite product with a pharmaceutically acceptable carrier.

* * * * *